United States Patent
Coles et al.

(10) Patent No.: US 12,159,241 B2
(45) Date of Patent: Dec. 3, 2024

(54) DEVICES AND PROCESSING SYSTEMS CONFIGURED TO ENABLE PHYSIOLOGICAL EVENT PREDICTION BASED ON BLEPHAROMETRIC DATA ANALYSIS

(71) Applicant: SDIP HOLDINGS PTY LTD, Victoria (AU)

(72) Inventors: Scott Coles, Queenscliff (AU); Trefor Morgan, Queenscliff (AU)

(73) Assignee: SDIP Holdings PTY LTD, Victoria (AU)

( * ) Notice: Subject to any disclaimer, the term of this patent is extended or adjusted under 35 U.S.C. 154(b) by 545 days.

(21) Appl. No.: 17/288,336

(22) PCT Filed: Oct. 23, 2019

(86) PCT No.: PCT/AU2019/051159
§ 371 (c)(1),
(2) Date: Apr. 23, 2021

(87) PCT Pub. No.: WO2020/082125
PCT Pub. Date: Apr. 30, 2020

(65) Prior Publication Data
US 2021/0378568 A1    Dec. 9, 2021

(30) Foreign Application Priority Data

Oct. 23, 2018   (AU) ................................ 2018904026
Oct. 23, 2018   (AU) ................................ 2018904027
(Continued)

(51) Int. Cl.
*G06N 5/00*    (2023.01)
*A61B 3/113*   (2006.01)
(Continued)

(52) U.S. Cl.
CPC ................ *G06N 5/04* (2013.01); *A61B 3/113* (2013.01); *A61B 3/14* (2013.01); *A61B 5/004* (2013.01);
(Continued)

(58) Field of Classification Search
CPC .......... G06N 5/04; G16H 50/20; G16H 40/63; G06V 10/40; G06V 20/597; G06V 40/193;
(Continued)

(56) References Cited

U.S. PATENT DOCUMENTS 6,246,344 B1   6/2001   Torch
7,071,831 B2   7/2006   Johns
(Continued)

FOREIGN PATENT DOCUMENTS

WO   2015/030797 A1   3/2015

OTHER PUBLICATIONS

IEEE (Towards Detection of Bus Driver Fatigue Based on Robust Visual Analysis of Eye State, Bappaditya Mandal, Liyuan Li, Gang Sam Wang, and Jie Lin, Mar. 2017) (Year: 2017).*
(Continued)

*Primary Examiner* — Khai M Nguyen
(74) *Attorney, Agent, or Firm* — TraskBritt

(57) ABSTRACT

Devices and processing systems are configured to enable physiological event prediction based on blepharometric data analysis. For example, some embodiments provide methods and associated technology that enable retrospective analysis of blepharometric data driving subsequent hardware/software configuration, thereby to provide for personalized and/or generalized biomarker identification.

14 Claims, 10 Drawing Sheets

(30) Foreign Application Priority Data

| Oct. 23, 2018 | (AU) | 2018904028 |
|---|---|---|
| Oct. 27, 2018 | (AU) | 2018904076 |
| Nov. 13, 2018 | (AU) | 2018904312 |
| Jan. 25, 2019 | (AU) | 2019900229 |

(51) Int. Cl.

| A61B 3/14 | (2006.01) |
|---|---|
| A61B 5/00 | (2006.01) |
| A61B 5/11 | (2006.01) |
| A61B 5/18 | (2006.01) |
| B60W 40/08 | (2012.01) |
| G06F 18/214 | (2023.01) |
| G06N 5/04 | (2023.01) |
| G06T 7/00 | (2017.01) |
| G06V 10/40 | (2022.01) |
| G06V 20/59 | (2022.01) |
| G06V 40/18 | (2022.01) |
| G16H 40/63 | (2018.01) |
| G16H 50/20 | (2018.01) |

(52) U.S. Cl.
CPC .......... *A61B 5/0077* (2013.01); *A61B 5/1103* (2013.01); *A61B 5/1118* (2013.01); *A61B 5/1128* (2013.01); *A61B 5/18* (2013.01); *A61B 5/4094* (2013.01); *A61B 5/4842* (2013.01); *A61B 5/6803* (2013.01); *A61B 5/6893* (2013.01); *A61B 5/7275* (2013.01); *A61B 5/7282* (2013.01); *A61B 5/746* (2013.01); *B60W 40/08* (2013.01); *G06F 18/214* (2023.01); *G06T 7/0012* (2013.01); *G06V 10/40* (2022.01); *G06V 20/597* (2022.01); *G06V 40/193* (2022.01); *G16H 40/63* (2018.01); *G16H 50/20* (2018.01); *A61B 2560/02* (2013.01); *B60W 2040/0872* (2013.01); *B60W 2540/221* (2020.02); *B60W 2540/223* (2020.02); *G06T 2207/20081* (2013.01); *G06T 2207/30041* (2013.01); *G06T 2207/30201* (2013.01); *G06T 2207/30268* (2013.01)

(58) Field of Classification Search
CPC ......... G06F 18/214; A61B 3/113; A61B 3/14; A61B 5/004; A61B 5/0077; 5/1103; A61B 5/1118; A61B 5/1128; A61B 5/18; A61B 5/4094; A61B 5/4842; A61B 5/6803; A61B 2560/02; B60W 40/08; B60W 2540/223; B60W 2540/221; B60W 2040/0872; G06T 7/0012; G06T 2207/20081; G06T 2207/30041; G06T 2207/30201; G06T 2207/30268
See application file for complete search history.

(56) References Cited

U.S. PATENT DOCUMENTS

| 7,791,491 | B2 | 9/2010 | Johns |
| 7,815,311 | B2 | 10/2010 | Johns et al. |
| 9,207,760 | B1 | 12/2015 | Wu et al. |
| 12,042,294 | B2* | 7/2024 | Krueger .................. A61B 3/14 |
| 2011/0077548 | A1 | 3/2011 | Torch |
| 2011/0216181 | A1 | 9/2011 | Yoda et al. |
| 2011/0295142 | A1 | 12/2011 | Chakravarthy et al. |
| 2011/0313259 | A1 | 12/2011 | Hatakeyama et al. |
| 2012/0072121 | A1 | 3/2012 | Mollicone et al. |
| 2012/0083700 | A1 | 4/2012 | Osorio |
| 2013/0022948 | A1 | 1/2013 | Angell et al. |
| 2013/0184997 | A1 | 7/2013 | Mott |
| 2013/0215390 | A1 | 8/2013 | Johns et al. |
| 2016/0019410 | A1 | 1/2016 | Komogortsev |
| 2016/0073874 | A1 | 3/2016 | Tsai et al. |
| 2016/0213298 | A1 | 7/2016 | Elsmore et al. |
| 2016/0216298 | A1 | 7/2016 | Campeanu et al. |
| 2017/0119248 | A1 | 5/2017 | Morgan et al. |
| 2017/0135577 | A1 | 5/2017 | Komogortsev |
| 2017/0337438 | A1 | 11/2017 | el Kaliouby, Jr. et al. |
| 2018/0247141 | A1* | 8/2018 | Mori ..................... B60K 28/06 |
| 2021/0378568 | A1* | 12/2021 | Coles ................... A61B 5/7267 |
| 2022/0254461 | A1* | 8/2022 | Vaughan ................. G06N 5/01 |
| 2023/0092866 | A1* | 3/2023 | Vaughan ................. G06N 5/01 |
| | | | 706/12 |

OTHER PUBLICATIONS

International Search Report for International Application No. PCT/AU2019-051159 dated Feb. 17, 2020, 9 pages.

International Written Opinion for International Application No. PCT/AU2019-051159 dated Feb. 17, 2020, 8 pages.

Mandal et al., Towards Detection of Bus Driver Fatigue Based on Robust Visual Analysis of Eye State, IEEE Transactions, vol. 18, No. 3, Mar. 2017, 545-557.

Da Conceicao et al., Blinking and Eyelid Myoclonia: Characteristics and Correlations of Eyelid Movements, Seizure, vol. 24, (2015(, pp. 12-16.

Jiang et al., Capturing and Evaluating Blinks from Video-Based Eyetrackers, Behav. Res. (2013), vol. 45, pp. 656-663.

Noman et al., Mobile-Based Eye-Blink Detection Performance Analysis on Android Platform, www.frontiersin.org, (Mar. 2018), vol. 5, Article 4, pp. 1-11/.

Paprocki et al., What Does Eye-Blink Rate Variability Dynamics Tess US About Cognitive Performance, Frontiers in Human Neuroscience, (Dec. 2017), vol. 11, Article 620, 99.1-9.

Siegle et al,, Blink Before and After you Think: Blinks Occur Prior to and Following Cognitive Load is Indexed by Pupillary Responses, Psychophysiology, 45, (2008), pp. 679-687.

Murray; Measuring Alertness; Sep. 8, 2006 (Year: 2006).

Burton David; Mobile Wearable Monitoring Systems; 2016 (Year: 2016).

Byrom et al. "Brain Monitoring Devices in Neuroscience Clinical Research: The Potential of Remote Monitoring Using Sensors, Wearables, and Mobile Devices." Clinical Pharmacology & Therapeutics, (Online Apr. 18), vol. 104, No. 1., pp. 59-71. (Year: 2018).

Nicolosi Robert; Botulinum Nanoemulsions; 2008 (Year: 2008).

Suzuki et al. "Measurement of Driver's Consciousness by Image Processing—A Method for Presuming Driver's Drowsiness by Eye-Blinks coping with Individual Differences." IEEE International Conference on Systems, Man and Cybernetics, Taipei, Taiwan, doi:10.1109/ICSMC.2006.385313, pp. 2891-2896. (Year: 2006).

* cited by examiner though written as a single document, the present disclosure relates, in various embodiments, to
DEVICES AND PROCESSING SYSTEMS CONFIGURED TO ENABLE PHYSIOLOGICAL EVENT PREDICTION BASED ON BLEPHAROMETRIC DATA ANALYSIS

CROSS-REFERENCE TO RELATED APPLICATIONS

This application is a national phase entry under 35 U.S.C. § 371 of International Patent Application PCT/AU2019/051159, filed Oct. 23, 2019, designating the United States of America and published as International Patent Publication WO 2020/082125 A1 on Apr. 30, 2020, which claims the benefit under Article 8 of the Patent Cooperation Treaty to Australian Patent Application Serial No. 2018904026, filed Oct. 23, 2018, Australian Patent Application Serial No. 2018904027, filed Oct. 23, 2018, Australian Patent Application Serial No. 2018904028, filed Oct. 23, 2018, Australian Patent Application Serial No. 2018904076, filed Oct. 27, 2018, Australian Patent Application Serial No. 2018904026, filed Nov. 13, 2018 and Australian Patent Application Serial No. 2019900229, filed Jan. 25, 2019.

TECHNICAL FIELD

The present disclosure relates, in various embodiments, to devices and processing systems configured to enable physiological event prediction based on blepharometric data analysis. For example, some embodiments provide methods and associated technology that enable retrospective analysis of blepharometric data driving subsequent hardware/software configuration, thereby to provide for personalised and/or generalised biomarker identification. While some embodiments will be described herein with particular reference to that application, it will be appreciated that the present disclosure is not limited to such a field of use, and is applicable in broader contexts.

BACKGROUND

Any discussion of the background art throughout the specification should in no way be considered as an admission that such art is widely known or forms part of common general knowledge in the field.

It is known to analyze neurological conditions from analysis of eyelid movements. For example, U.S. Pat. No. 7,791,491 teaches a method and apparatus for measuring drowsiness based on the amplitude to velocity ratio for eyelids closing and opening during blinking as well as measuring duration of opening and closing. This enables an objective measurement of drowsiness.

BRIEF SUMMARY

Through research into relationships between eye and eyelid movement parameters and neurological conditions, opportunities for probabilistic prediction and/or detection of additional neurological and/or other physiological conditions via analysis of eyelid movement parameters have been identified.

It is an object of the present disclosure to overcome or ameliorate at least one of the disadvantages of the prior art, or to provide a useful alternative.

One embodiment provides a method for processing blepharometric data for a subject, the method including:

(i) receiving input representative of an observed occurrence of a physiological event or condition;
(ii) identifying a set of baseline blepharometric data artefacts data for the subject;
(iii) extracting a set of event blepharometric data artefacts for the subject for a period preceding and/or including the observed occurrence of a physiological event or condition;
(iv) comparing the baseline blepharometric data artefacts with the event blepharometric data artefacts, thereby to identify one or more anomaly artefacts; and
(v) performing an anomaly artefact analysis process thereby to selectively define a candidate blepharometric data indicator for the subject.

One embodiment provides a method wherein the input representative of an observed occurrence of a physiological event or condition includes timestamped data representative of an event or condition identified by a separate monitoring system.

One embodiment provides a method wherein the separate monitoring system includes a brain activity monitoring system.

One embodiment provides a method wherein the separate monitoring system includes a cardiovascular activity monitoring system.

One embodiment provides a method wherein the separate monitoring system includes a monitoring system that receives results from an interactive test.

One embodiment provides a method wherein the input representative of an observed occurrence of a physiological event or condition includes timestamped data representative of an event or condition identified manually and inputted via in input interface.

One embodiment provides a method wherein the set of baseline blepharometric data artefacts data for the subject are maintained by a blepharometric data management system that collects blepharometric data for the subject thereby to define and maintain the set of baseline blepharometric data artefacts data.

One embodiment provides a method wherein the blepharometric data management system receives blepharometric data from one or more of the following sources:

wearable configurations including infrared reflectance oculography components;
vehicle operator configurations, in which an image capture device is positioned to capture blepharometric data for an operator of the vehicle;
desktop/laptop computer configurations in which a webcam or other image capture device is used to monitor subject blepharometric data subject to: (i) a foreground software application; and/or (ii) a background software application, which collects blepharometric data whilst a subject engages in other activities on the computer;
mass transport passenger configurations in which an image capture device operates in conjunction with a display screen, such that blepharometric data is collected concurrently with the subject observing content displayed via the display screen;
vehicle passenger configurations in which an image capture device is positioned to capture blepharometric data for a passenger of the vehicle;
smartphone/tablet configurations in which a front facing camera is used to monitor subject blepharometric data, subject to: (i) a foreground application; and/or (ii) a background application, which collects blepharometric data whilst a subject engages in other activities on the smartphone/tablet; and medical facility configurations.

One embodiment provides a method wherein the step of extracting a set of event blepharometric data artefacts for the subject for a period preceding and/or including the observed occurrence of the physiological event or condition includes:
identifying a timestamp associated with the physiological event or condition;
identifying a set of blepharometric data for the subject stored in a database having timestamps for a predefined period preceding and/or including the observed occurrence of the physiological event or condition; and
extracting that blepharometric data for from the database.

One embodiment provides a method wherein the set of blepharometric data is defined as eyelid position against time, and the method additionally includes processing the set of blepharometric data thereby to extract blepharometric data artefacts, thereby to define the set of event blepharometric data artefacts.

One embodiment provides a method wherein the blepharometric data artefacts include any one or more of the following:
Measurements defined by, or representative of statistical attributes of, blink total duration (BTD);
Measurements defined by, or representative of statistical attributes of, inter-event duration (IED);
Measurements defined by, or representative of statistical attributes of, blink amplitudes;
Measurements defined by, or representative of statistical attributes of, eyelid velocities;
Measurements defined by, or representative of statistical attributes of, amplitude to velocity ratios for blink events;
Measurements defined by, or representative of statistical attributes of, negative inter-event duration (negative IED);
Blink event counts, including blink event counts for a set of blink events having defined attributes occurring within a defined time period;
Measurements defined by, or representative of statistical attributes of, blink eye closure duration (BECD); and
Measurements defined by, or representative of statistical attributes of, duration of ocular quiescence (DOQ).

One embodiment provides a method wherein comparing the baseline blepharometric data artefacts with the event blepharometric data artefacts, thereby to identify one or more anomaly artefacts includes: identifying one or more event blepharometric data artefacts having values outside of a threshold deviation from corresponding blepharometric data artefacts defined in the baseline blepharometric data artefacts One embodiment provides a method wherein performing an anomaly artefact analysis process thereby to selectively define a candidate blepharometric data indicator for the subject includes: determining presence of the identified anomaly artefact in blepharometric data maintained in respect of one or more other subjects.

A method according to any preceding claim wherein performing an anomaly artefact analysis process thereby to selectively define a candidate blepharometric data indicator for the subject includes: determining whether the blepharometric data artefact is likely to have been caused by physical conditions of the subject unrelated to the observed occurrence of a physiological event or condition.

A method according to any preceding claim wherein performing an anomaly artefact analysis process thereby to selectively define a candidate blepharometric data indicator for the subject includes: determining presence of the identified anomaly artefact in blepharometric data in blepharometric data for the same subject where the same form of occurrence of a physiological event or condition has been observed.

A method according to any preceding claim wherein the set of event blepharometric data artefacts for the subject for a period preceding and/or including the observed occurrence of a physiological event or condition are collected via infrared reflectance oculography hardware.

A method according to any preceding claim wherein the set of event blepharometric data artefacts for the subject for a period preceding and/or including the observed occurrence of a physiological event or condition are collected via camera-based blepharometric data monitoring.

A system according to any preceding claim including configuring one or more blepharometric data monitoring systems to monitor for presence of the candidate blepharometric data artefact in subsequent blepharometric data collected from the subject.

In some embodiments, the method further includes providing an alert that the occurrence of a physiological event or condition of the same nature as the observed occurrence of a physiological event or condition is possible, and providing an interface that is configured to enable reporting on subsequent observation or non-observation of the possible occurrence.

In some embodiments, the one or more blepharometric data monitoring systems include at least one blepharometric data monitoring system that is configured to uniquely identify the subject.

Reference throughout this specification to "one embodiment," "some embodiments" or "an embodiment" means that a particular feature, structure or characteristic described in connection with the embodiment is included in at least one embodiment of the present disclosure. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the present disclosure will now be described, by way of example only, with reference to the accompanying drawings in which.

DETAILED DESCRIPTION

Figure 1A:
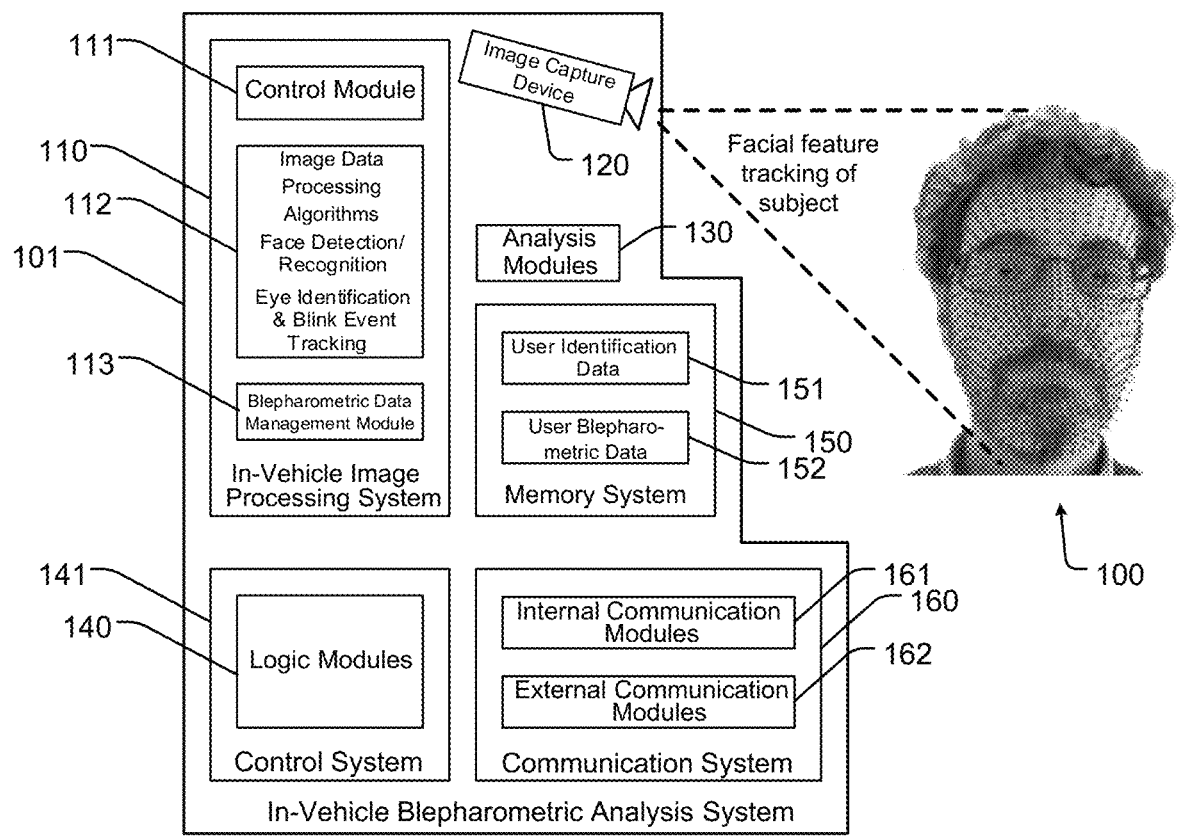
FIG. 1A illustrates an in-vehicle blepharometric data collection/monitoring system according to one embodiment.

The present disclosure relates, in various embodiments, to devices and processing systems configured to enable physiological event prediction based on blepharometric data analysis. For example, some embodiments provide methods and associated technology that enable retrospective analysis of blepharometric data driving subsequent hardware/software configuration, thereby to provide for personalized and/or generalized biomarker identification.

Overview and Context

A human subject's involuntary blinks and eyelid movements are influenced by a range of factors, including the subject's behavioural state and brain function. For example, this has been used in the past for detection of drowsiness. More broadly, analysis of data derived from eye and eyelid movements can be performed thereby to identify data artefacts, patterns and the like, and these are reflective of the subject's behavioural state, brain function and the like.

A number of eyelid-based monitoring systems are known. For example, these include technology that is configured to detect blinks, and technology that is configured to monitor eyelid movement (also referred to as "blepharon movement" or "blepharonic movement").

The technology described herein is focussed on collection and analysis of "blepharometric data," with the term "blepharon" describing a human eyelid. The term "blepharometric data" is used to define data that describes eyelid movement as a function of time. For example, eyelid position may be recorded as an amplitude. Eyelid movements are commonly categorized as "blinks" or "partial blinks." The term "blepharometric data" is used to distinguish technology described herein from other technologies that detect the presence of blinks for various purposes. The technology herein is focused on analyzing eyelid movement as a function of time, typically measured as an amplitude. This data may be used to infer the presence of what would traditionally be termed "blinks"; however, it is attributes of "events" and other parameters identifiable in eyelid movements, which are of primary interest to technologies described herein. Events and other parameters that are identified from the processing of blepharometric data are referred to as "blepharometric artefacts." These are referred to as "blepharometric artefacts," with such artefacts being identifiable by application of various processing algorithms to a data set that described eyelid position as a function of time (i.e., blepharometric data). For example, the artefacts may include:

Blink total duration (BTD), which is preferably measured as a time between commencement of closure movement that exceeds a defined threshold and completion of subsequent opening movement.

Blink rates.

Amplitude to velocity ratios (AVRs).

Negative Inter-Event-Duration (IED) (discussed in detail further below).

Positive IED

Negative AVR (i.e., during closure)

Positive AVR (i.e., during re-opening)

AVR Product (negative AVR*positive AVR)

AVR ratio (negative AVR divided by positive AVR)

BECD (blink eye closure duration).

Negative DOQ (duration of ocular quiescence)

Positive DOQ

Relative Amplitude

Relative Position

Maximum Amplitude

Maximum Velocity

Negative zero crossing index (ZCI).

Pos ZCI

Blink start position

Blink end position

Blink start time

Blink end time

Trends and changes in any of the above artefacts over a defined period.

The determination of blepharometric artefacts may include any one or more of:

Determination of a time period from blink initiation to blink completion (also referred to as a blink duration or blink length). Blink initiation and blink completion may be determined based on a determined "inter-blink" eyelid amplitude range, with movement outside that amplitude range being categorized as a blink.

Determination time period between blinks, optionally measured between blink initiation times for consecutive blinks.

Analysis of "events," including relative timing of events, with an "event" being defined as any positive or negative deflection that is greater than a given velocity threshold for a given duration. In this regard, a "blink" is in some embodiments defined as the pairing of positive and negative events that are within relative amplitude limits and relative position limits. There may be multiple events within a given blink, when an eyelid is outside of an "inter-blink" eyelid amplitude range.

a time period for eye closure motion;

a time period during which the eye is closed;

a time period for eye re-opening motion;

velocity measurements (which include velocity estimation measurements) for eye closure motion and/or eye re-opening motion. are also made, which may be used for the purposes of determining amplitude-to-velocity ratios.

Known eyelid movement monitoring systems (also referred to herein as blepharometric data monitoring systems) focus on point-in-time subject analysis. For example, commonly such technology is used as a means for assessing subject alertness/drowsiness at a specific moment, potentially benchmarked against known data for a demographically relevant population. However, benchmarking against a demographically population is by no means ideal from an analysis perspective, as blepharometric data biomarkers may be individually variant across a population.

A solution proposed herein makes use of a blepharometric data collection and analysis system that is configured to enable data tagging of physiological events (for example, point-in-time events such as seizures) and/or physiological conditions (for example, conditions associated with high performance or low performance in a cognitive and/or athletic capacity). This is used to allow subsequent configuration of blepharometric data monitoring hardware to perform predictions of future events and/or conditions.

This solution optionally leverages blepharometric data collection systems that are deployed in a range of human environments, being environments in which humans are commonly positioned suitably for blepharometric data collection. Examples considered herein are vehicles (for example, cars, aeroplanes, trains, and the like), computing devices (for example, smartphones, tablets, and PCs), and other locations. This allows long term blepharometric data collection on an individualised basis, allowing for better management of neurological health (and other factors such as safety). For instance, specific use cases might include providing warnings in advance of seizures, informing a person of a risk of a degenerative brain illness, detection of brain injuries from accidents and/or sporting activities, and personalised detection of unusual levels of drowsiness. Blepharometric data may alternately and/or additionally be collected via more conventional blepharometric data monitoring hardware, for example, head-wearable units (for example, spectacles) that make use of infrared reflectance oculography.

In some embodiments, technology is adapted to enable differentiation between voluntary and involuntary eyelid movements, using known attributes, which are markers for voluntary movements. In this regard, some embodiments apply filters thereby to limit analysis to either or both of voluntary and involuntary movements. For instance, some embodiments that consider only involuntary eyelid movements apply filters thereby to exclude detected voluntary blinks from analysis.

In terms of behavioural state, there are many factors that have an effect on involuntary eyelid movements, with examples including: a subject's state of physical activity; a subject's posture; other aspects of a subject's positional state; subject movement; subject activity; how well slept the subject happens to be; levels of intoxication and/or impairment; and others. In terms of brain function, factors that have effects on involuntary eyelid movements include degenerative brain injuries (e.g., Parkinson's disease) and traumatic brain injuries.

Example Methodology

Figure 3:
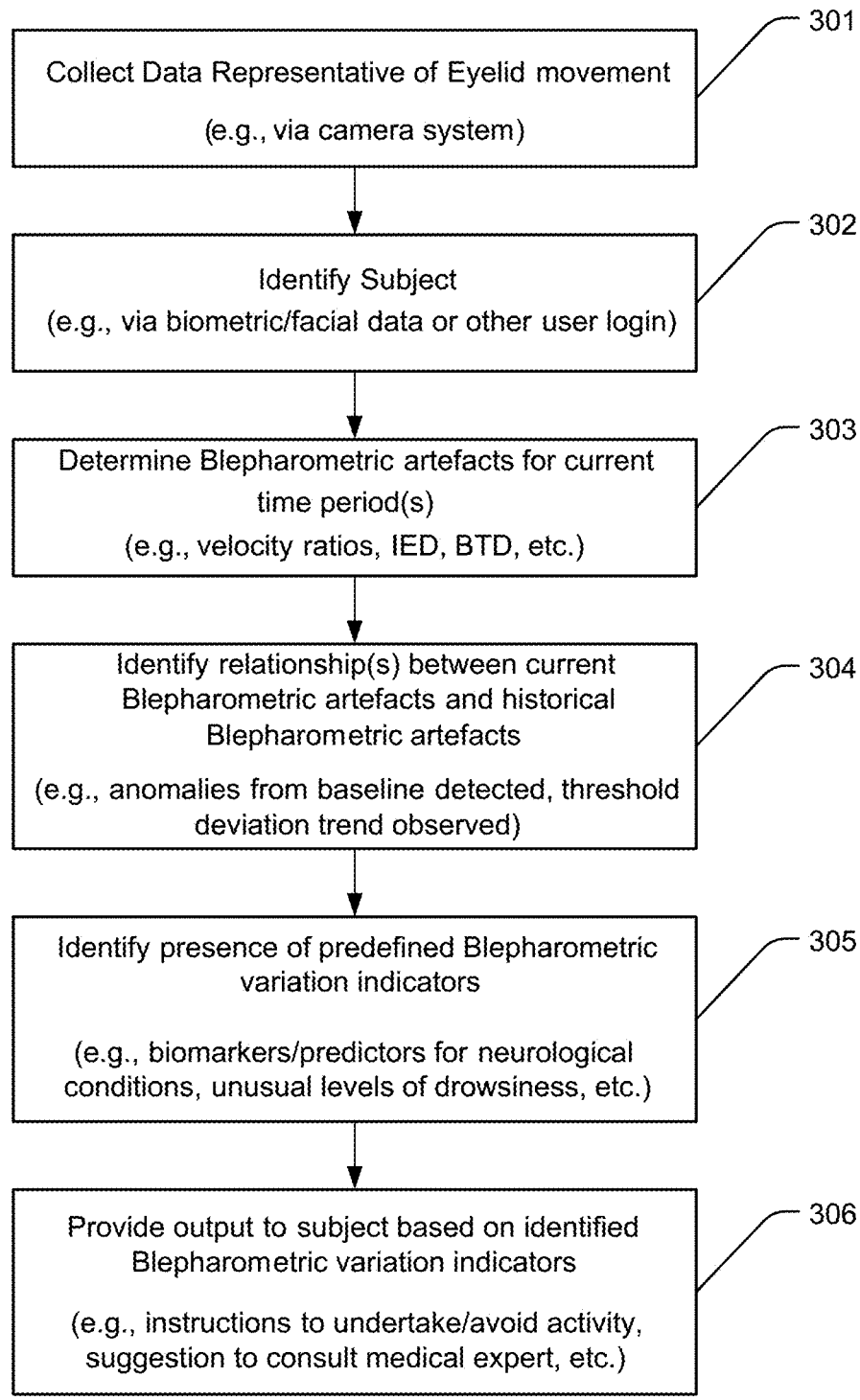
FIG. 3 illustrates a method according to one embodiment.

FIG. 3 illustrates a high-level methodology, which is relevant to a range of embodiments discussed below. This methodology, depending on the specific hardware implementation used by a given embodiment, is optionally performed via software modules executing across a plurality of connected devices, for example, including local devices (for example, computing devices housed in a vehicle and/or user's mobile devices such as smartphones) and Internet-connected server devices (also referred to as "cloud" components). It should be appreciated that any computing devices and computer-executed methods configured for the purposes of enabling the overall performance of a methodology based on those described below by reference to FIG. 3 forms embodiments of disclosures for the purposes of this specification.

Block 301 represents a process including collecting data representative of eyelid movement. For the majority of embodiments described below, this is achieved via a camera system having an image capture component that is positioned into a capture zone in which a subject's face is predicted to be positioned. For example, this may include:

Vehicles, including passenger vehicles or operator-only vehicles, wherein the image capture component is positioned to capture a region in which an operator's face is predicted to be contained during normal operation. For example, in the case of an automobile, the image capture component may include a camera mounting in or adjacent a dashboard or windscreen.

Vehicles, in the form of passenger vehicles, wherein the image component is positioned to capture a region in which a passenger's face is predicted to be contained during normal operation. For example, in the case of an automobile, the image capture component may include a camera mounting in or adjacent a dashboard or windscreen, the rear of a seat (including a seat headrest), and so on.

Mass transport vehicles, including passenger trains and/or aircraft, wherein the image component is positioned to capture a region in which a passenger's face is predicted to be contained during normal operation. For example, the image capture component may be mounted in the rear of a seat (including a seat headrest), optionally in a unit that contains other electronic equipment such as a display monitor.

Seating arrangements, such as theatres, cinemas, auditoriums, lecture theatres, and the like. Again, mounting image capture components in the rear of seats is an approach adopted in some embodiments.

The data that is captured is not limited to data captured for the purposes of extended monitoring and analysis of subject neurological factors via blepharometric data collection. For example, in some embodiments that is one purpose, and there is an alternate purpose, which is optionally point-in-time based. For example, point-in-time drowsiness detection is relevant in many of the above scenarios. Furthermore, whilst embodiments below focus on individualized blepharometric data collection and/or monitoring, collected blepharometric data is optionally additionally collected for the purposes of group monitoring/analysis (including where blepharometric data is anonymised such that it is not attributable to a specific individual). For example, this may be used in the context of seating arrangements to assess overall student/viewer attention/drowsiness, or in the context of aeroplanes and other mass transport to perform analysis of passenger health factors.

Block 302 represents a process including identifying a subject from whom the blepharometric data collected at block 301 originates. This optionally includes:

Credential-based identification, for example, via a login. This may include pairing of a personal device (such as a smartphone) to blepharometric data monitoring system (e.g., pairing a phone to an in-vehicle system), inputting login credentials via an input device, or other means.

Biometric identification. For example, in some embodiments described herein a camera-based blepharometric data monitoring system utilises image data to additionally perform facial recognition functions, thereby to uniquely identify human subjects.

Other forms of identification.

Identification of the subject is relevant for the purposes of comparing current blepharometric data with historical blepharometric data for the same subject. For example, in some embodiments an analysis system has access to a database of historical blepharometric data for one subject (for example, where the system is installed in a vehicle and monitors only a primary vehicle owner/driver) or multiple subjects (for example, a vehicle configured to monitor multiple subjects, or a cloud-hosted system that received blepharometric data from a plurality of networked systems, as described further below).

Block 303 represents a process including determination of blepharometric data artefacts for a current time period. For example, the artefacts may include:
Blink total duration (BTD).
Blink rates.
Amplitude to velocity ratios (AVRs).
Negative Inter-Event-Duration (IED).
Positive IED.
Negative AVR (i.e., during closure)
Positive AVR (i.e., during re-opening)
AVR Product (negative AVR*positive AVR)
AVR ratio (negative AVR divided by positive AVR)
BECD (blink eye closure duration).
Negative DOQ (duration of ocular quiescence)
Positive DOQ
Relative Amplitude
Relative Position
Max Amplitude
Max Velocity
Neg ZCI (zero crossing index)
Pos ZCI
Blink start position
Blink end position
Blink start time
Blink end time
Trends and changes in any of the above artefacts over the period.

The "current period" may be either a current period defined by a current user interaction with a blepharometric data monitoring system, or a subset of that period. For instance, in the context of a vehicle, the "current period" is in one example defined as a total period of time for which a user operates the vehicle and has blepharometric data monitored, and in another embodiment is a subset of that time. In some embodiments multiple "current periods" are defined, for example, using time block samples of between two and fifteen minutes (which are optionally overlapping), thereby to compare blepharometric data activity during periods of varying lengths (which may be relevant for differing neurological conditions, which, in some cases, present themselves based on changes in blepharometric data over a given period of time).

The current blepharometric data may be used for point-in-time neurological conditional analysis, for example, analysis of subject alertness/drowsiness, prediction of seizures, detection of seizures, and other such forms of analysis. Specific approaches for analysing blepharometric data thereby to detect/predict particular neurological conditions fall beyond the scope of the present disclosure.

Block 304 represents a process including identification of relationships between current blepharometric data artefacts and historical blepharometric data artefacts. This allows for artefacts extracted in the current blepharometric data to be given context relative to baselines/trends already observed for that subject. The concept of "identification of relationships" should be afforded a broad interpretation to include at least the following:

Identification of long-term trends. For example, blepharometric data collected over a period of weeks, months or years may be processed thereby to identify any particular blepharometric data artefacts that are evolving/trending over time. In some embodiments, algorithms are configured to monitor such trends, and these are defined with a set threshold for variation, which may be triggered in response to a particular set of current blepharometric data.

Identification of current point-in-time deviations from baselines derived from historical blepharometric data. For example, current data may show anomalous spiking in particular artefacts, or other differences from baselines derived from the subject's historical blepharometric data, which may give rise for concern. By way of example, this form of analysis may be used to determine/predict the presence of: (i) onset of a neurological illness or degenerative condition; (ii) presence of a brain injury, including a traumatic brain injury; (iii) impairment by alcohol, drugs, or other physical condition; (iv) abnormal levels of drowsiness; or (v) other factors.

In relation to onset of a neurological illness or degenerative condition, this may include either or both of short term onsets (e.g., onset of neurological diseases and neurological condition such as strokes and/or seizures and long term onsets (for example, long term detection rather than the short term is more appropriate, for example, such as Alzheimer's, Parkinson's, Multiple Sclerosis, and Muscular Dystrophy).

Block 305 represents a process including identification of presence of one or more blepharometric data variation indicators, for example, based on the identification of relationships at block 304. These indicators may be used to allow data-based determination/prediction of the presence of: (i) onset of a neurological illness or degenerative condition; (ii) presence of a brain injury, including a traumatic brain injury; (iii) impairment by alcohol, drugs, or other physical condition; (iv) abnormal levels of drowsiness; or (v) other factors. By way of example, rules are defined that associate a data relationship (for example, deviation from baseline values, a trend identification, or the like) with a prediction on neurological condition. These may be defined, for example, using logical structures, such as If current 15-minute standard deviation of negative IED deviates by over 20% of the determined baseline 15-minute standard deviation of negative IED, raise alert X.

If current 1-minute average amplitude-to-velocity ratio greater than 40% of baseline 1-minute average amplitude-to-velocity ratio, raise alert Y.

If current data causes greater than 20% downward trend in artefact set A, comprising defined grouping of multiple blepharometric data artefacts, then raise alert Z.

It should be appreciated that these are examples only, and that the present disclosure is directed to hardware and software that enables the implementation of such analysis/alert processes, as opposed to those processes themselves.

Block 306 represents a process including providing output to the human subject based on identified blepharometric data variation indicators. This may include an instruction/suggestion to avoid a particular activity (such as driving), an instruction/suggestion to undertake a particular activity (such as medication, resting, walking around, or the like), or a suggestion to consult a medical expert about a potential neurological condition. The manner by which the output is delivered varies depending on both the nature of the alert/condition, and the hardware environment in place. Examples range from the sending of emails or other messages or the display of information on a local device (for example, an in-vehicle display).

Various hardware/software embodiments configured to enable the above methodology are described below.

Example In-Vehicle Blepharometric Data Monitoring System

FIG. 1A illustrates an example in-vehicle blepharometric data monitoring system. Whilst it is known to provide a blepharometric data monitoring system in a vehicle for the purposes of point-in-time analysis of alertness/drowsiness, the system of FIG. 1A provides for substantial advances in ability to perform analysis of a user's neurological condition by way of providing a memory module that stores historical blepharometric data, and enables analysis of changes in blepharometric data for the user over time.

The system of FIG. 1A includes an image capture device 120. This may include substantially any form of appropriately sized digital camera, preferably a digital camera with a frame rate of over 60 frames per second. Higher frame rate cameras are preferred, given that with enhanced frame rate comes an ability to obtain higher resolution data for eyelid movement.

Device 120 is positioned to capture a facial region of a subject. Device 120 is in one embodiment installed in a region of a vehicle in the form of an automobile, for example, on or adjacent the dashboard, windscreen, or visor, such that it is configured to capture a facial region of a driver. In another embodiment device 120 is positioned on or adjacent the dashboard, windscreen, or visor, such that it is configured to capture a facial region of a front seat passenger. In another embodiment device 120 is positioned in a region such as the rear of a seat such that it is configured to capture a facial region of a back-seat passenger. In some embodiments a combination of these are provided, thereby to enable blepharometric data monitoring for both a driver and one or more passengers.

Although the system of FIG. 1A (and other systems) are described by reference to a vehicle in the form of an automobile, it will be appreciated that a system as described is also optionally implanted in other forms of vehicles, including mass-transport vehicles such as passenger airplanes, busses/coaches, and trains. In such embodiments there are preferably one or more analysis systems each supporting a plurality of image capture devices, each positioned to capture a respective passenger.

An in-vehicle image processing system 110 is configured to receive image data from image capture device 120 (or multiple devices 120), and process that data thereby to generate blepharometric data. A control module 111 is configured to control device 120, operation of image data processing, and management of generated data. This includes controlling operation of image data processing algorithms, which are configured to:

(i) Identify that a human face is detected.

(ii) In embodiments where subject identification is achieved via facial recognition algorithms (which is not present in some embodiments, for example, embodiments that identify a subject via alternate means), perform a facial recognition process thereby to identify the subject. This may include identifying a known subject based on an existing subject record defined in user identification data 151 stored in a memory system 150, or identifying an unknown subject and creating a new subject user identification data 151 stored in a memory system 150.

(iii) In a detected human face, identifying an eye region. In some embodiments the algorithms are configured to track one eye region only; in other embodiments both eye regions are tracked thereby to improve data collection.

(iv) Identify, in the eye region(s), presence and movement of an eyelid. For example, in a preferred embodiment this is achieved by way of recording an eyelid position relative to a defined "open" position against time. This allows generation of blepharometric data in the form of eyelid position (amplitude) over time. It will be appreciated that such data provides for identification of events (for example, blink events) and velocity (for example, as a first derivative of position against time). In a preferred embodiment, a facial recognition algorithm is used to enable identification of: (i) a central position on an upper eyelid on a detected face; and (ii) at least two fixed points on the detected face. The two fixed points on the detected face are used to enable scaling of measurements of movement of the central position of the upper eyelid thereby to account to changes in relative distance between the user and the camera. That is, a distance between the two fixed points is used as a means to determine position of the face relative to the camera, including position by reference to distance from the camera (as the user moves away, the distance between the fixed points decreases).

Algorithms 112 optionally operate to extract additional artefacts from blepharometric data, for example, amplitude-velocity rations, blink total durations, inter-event durations, and the like. It will be appreciated; however, that extraction of such artefacts may occur in downstream processing.

A blepharometric data management module 113 is configured to coordinate storage of blepharometric data generated by algorithms 112 in user blepharometric data 152. This includes determining a user record against which blepharometric data is to be recorded (in some cases there is only a single user record, for example, where blepharometric data s collected only from a primary driver of an automobile). In some embodiments, the function of the blepharometric data management module 113 includes determining whether a set of generated blepharometric data meets threshold data quality requirements for storage, for example, based on factors including a threshold unbroken time period for which eyelid tracking is achieved and blepharometric data is generated.

Memory system 150 includes user identification data 151 for one or more users. As noted, in some embodiments, system 101 is configured to collect and analyse blepharometric data for only a single user (for instance, the primary driver of a vehicle) and includes identification data to enable identification of only that user. In other embodiments, system 101 includes functionality to collect and analyse blepharometric data for multiple users, and includes identification data to enable identification of any of those users (and optionally, as noted above, defining of a new record for a previously unknown user). The identification data may include login credentials (for example, a user ID and/or password) which are inputted via an input device. Alternately, the identification data may be biometric, for example, using facial recognition as discussed above or an alternate biometric input (such as a fingerprint scanner). In some embodiments, this leverages an existing biometric identification system of the vehicle.

User blepharometric data 152 includes data associated with identified users, the data basing time coded thereby to enable identification of a date/time at which data was collected. The blepharometric data stored in data 152 optionally includes blepharometric data generated by algorithms 112 and further blepharometric data derived from further processing of that data, for example, data representing average periodic IEDs and/or BTDs, and other relevant statistics, which may be determined over time. In some embodiments, data processing algorithms are updated over time, for example, to allow analysis of additional biomarkers determined to be representative of neurological conditions that require extraction of particular artefacts from blepharometric data.

Analysis modules 130 are configured to perform analysis of user blepharometric data 152. This includes executing a process including identification of relationships between current blepharometric data artefacts (e.g., data recently received from in-vehicle image processing system 110) and historical blepharometric data artefacts (e.g., older data pre-existing in memory system 150). This allows for artefacts extracted in the current blepharometric data to be given context relative to baselines/trends already observed for that subject. The concept of "identification of relationships" should be afforded a broad interpretation to include at least the following:

- Identification of long-term trends. For example, blepharometric data collected over a period of weeks, months or years may be processed thereby to identify any particular blepharometric data artefacts that are evolving/trending over time. In some embodiments, algorithms are configured to monitor such trends, and these are defined with a set threshold for variation, which may be triggered in response to a particular set of current blepharometric data.
- Identification of current point-in-time deviations from baselines derived from historical blepharometric data. For example, current data may show anomalous spiking in particular artefacts, or other differences from baselines derived from the subject's historical blepharometric data, which may give rise for concern. By way of example, this form of analysis may be used to determine/predict the presence of: (i) onset of a neurological illness or degenerative condition; (ii) presence of a brain injury, including a traumatic brain injury; (iii) impairment by alcohol, drugs, or other physical condition; (iv) abnormal levels of drowsiness; or (v) other factors.

Analysis modules are optionally updated over time (for example, via firmware updates or the like) thereby to allow for analysis of additional blepharometric data artefacts and hence identification of neurological conditions. For example, when a new method for processing blepharometric data thereby to predict a neurological condition based on a change trend in one or more blepharometric data artefacts, an analysis algorithm for that method is preferably deployed across a plurality of systems such as system 101 via a firmware update or the like.

System 101 additionally includes a communication system 160, which is configured to communicate information from system 101 to human users. This may include internal communication modules 161 which provide output data via components installed in the vehicle, for example, an in-car display, warning lights, and so on. External communication modules 162 are also optionally present, for example, to enable communication of data from system 101 to user devices (for example, via Bluetooth, Wi-Fi, or other network interfaces), optionally by email or other messaging protocols. In this regard, communication system 160 is configured to communicate results of analysis by analysis modules 130.

A control system 140 included logic modules 141, which control overall operation of control system 140. This includes execution of logical rules thereby to determine communications to be provide din response to outputs from analysis modules 130. For example, this may include:
- An in-vehicle notification in the event that a threshold level of drowsiness is detected.
- An in-vehicle notification of another neurological condition.
- An in-vehicle notification with an alert code that is to be inputted into an online system thereby to obtain further information regarding a detected/predicted neurological condition.
- An external communication to a device/address defined in user identification data 151.

It will be appreciated that these are examples only, and logic modules 141 are able to provide a wide range of functionalities thereby to cause system 101 to act based on determinations by analysis modules 130.

It should be appreciated that the system illustrated in FIG. 1 provides technology whereby one or more digital camera is able to be installed in a vehicle, such as an automobile or mass transport vehicle, thereby to: (i) collect blepharometric data for an operator and/or one or more passengers; and (ii) enable determination of relationships between blepharometric data collected in a "current" period (for example, a last data set, a last day, a last week, or a last month) with historical blepharometric data that is stored for that same user. This allows for functionalities including, but not limited to:

- User-personalised drowsiness detection, based on detection of drowsiness-related blepharometric data artefacts that are beyond a threshold deviation from average values for a particular user;
- Prediction of neurological conditions, based on sudden changes and/or long term trends in change for one or more blepharometric data artefacts that are known to be indicative of particular neurological conditions;
- Personalised prediction of future neurological conditions, for example, prediction of future drowsiness based on known drowsiness development patters extracted for the individual from historical data, and prediction of likelihood of a seizure based on individually-verified seizure prediction biomarkers identifiable in blepharometric data.
- Identification of point-in-time relevant neurological conditions based on sudden deviations from historical averages, which may be representative of sudden neurological changes, for example, traumatic brain injuries (e.g., concussion) and/or impairment based on other factors (such as medications, drugs, alcohol, illness, and so on).

Figure 1B:
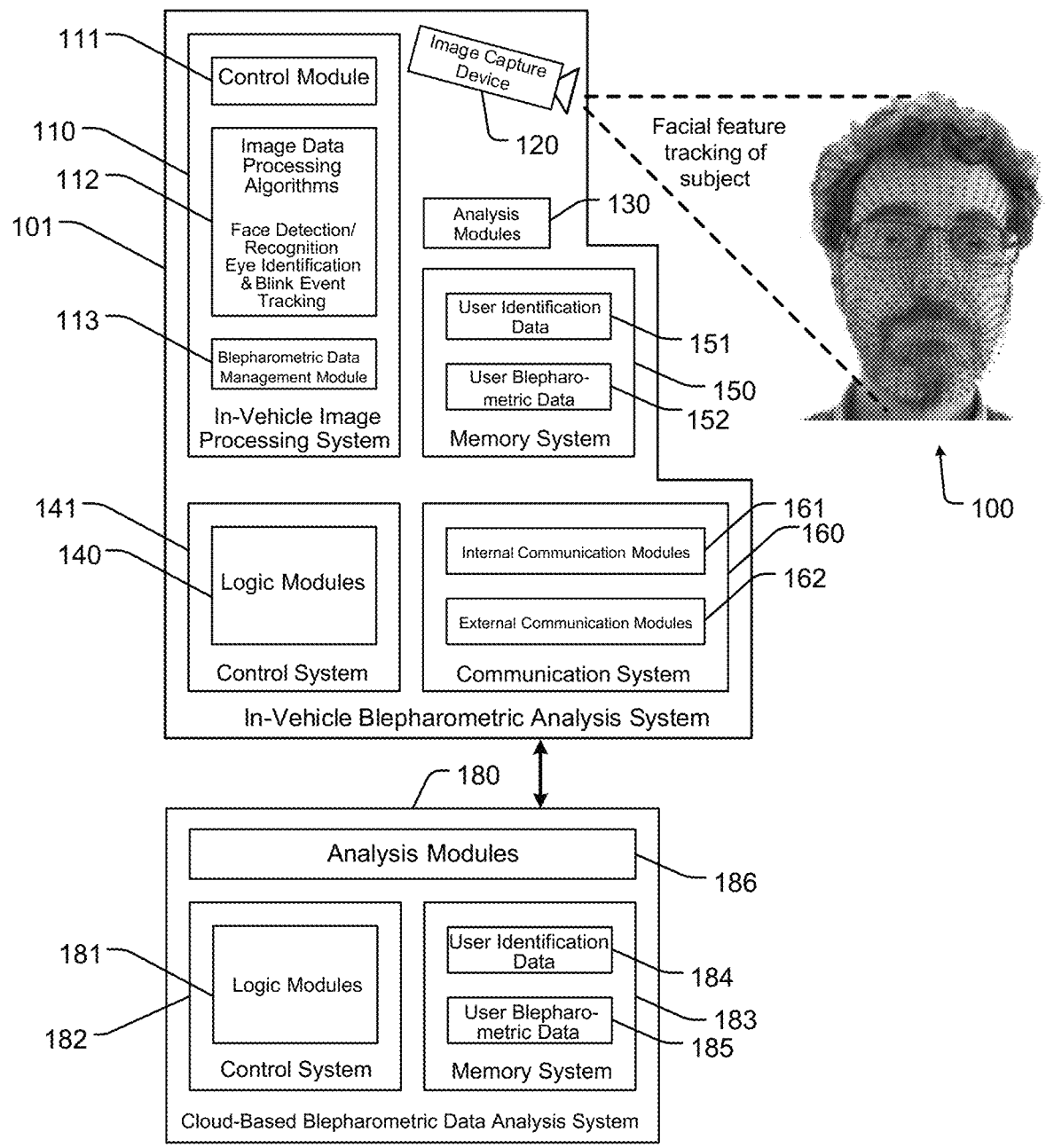
FIG. 1B illustrates an in-vehicle blepharometric data collection/monitoring system according to one embodiment.

Example In-Vehicle Blepharometric Data Monitoring Systems, with Cloud-Based Analysis FIG. 1B illustrates a further embodiment, which includes various common features with the embodiment illustrated in FIG. 1A. On general terms, in some embodiments, external communication modules 162 facilitate communication with a remote server device, which optionally performs additional blepharometric data analysis. In the example of FIG. 1B, external communication modules 162 enable communication between system 101 and a cloud-based blepharometric data analysis system 180.

System 180 includes a control system 182 and logic modules 181, which are provided by computer executable code executing across one or more computing devices thereby to control and deliver functionalities of system 180.

System 180 additionally includes a memory system 183, which includes user identification data 184 and user blepharometric data 185. The interplay between memory system 183 and memory system 150 varies between embodiments, with examples discussed below:

- In some embodiments, memory system 150 operates in parallel with memory system 183, such that certain records are synchronised between the systems based on a defined protocol. For example, this optionally includes a given memory system 150 maintaining user blepharometric data and user identification data for a set of subjects that have presented at that in-vehicle system, and that data is periodically synchronised with the cloud system. For example, upon an unrecognised user presenting at a given in-vehicle system, the system optionally performs a cloud (or other external) query thereby to obtain identification data for that user, and then downloads from the cloud system historical user blepharometric data for that user. Locally collected blepharometric data us uploaded to the server. This, and other similar approaches, provide for transportability of user blepharometric data between vehicles.
- In some embodiments, memory system 150 is used primarily for minimal storage, with memory system 183 providing a main store for user blepharometric data. For example, in one example, memory system 150 includes data representative of historical blepharometric data baseline values (for instance, defined as statistical ranges), whereas detailed recordings of blepharometric data is maintained in the cloud system. In such embodiments, analysis modules 186 of cloud system 180 performed more complex analysis of user blepharometric data thereby to extract the historical blepharometric data baseline values, which are provided to memory system 150 where a given user is present or known thereby to facilitate local analysis of relationships from baselines.
- In some embodiments, local memory system 150 is omitted, with all persistent blepharometric data storage occurring in cloud memory system 183.

System 180 additionally includes analysis modules 186, which optionally perform a similar role analysis modules 130 in FIG. 1A. In some embodiments, local and cloud analysis modules operate in a complementary factor, for example, with analysis modules 130 performing relationship analysis relevant to point-in-time factors (for example, an altered/non-standard neurological state for a user by comparison with historical baselines, which warrants immediate intervention) and analysis modules 186 performing what is often more complex analysis of trends over time (which may be representative of degenerative neurological illnesses and the like) and do not require local immediate intervention in a vehicle. It will be appreciated that there exist a range of approaches for sharing processing (and memory storage) functions between an in-vehicle system and a cloud system, and configuration of thee is optionally determined based on considerations such as network speeds/bandwidth, along with local memory and storage resource availability.

There are various advantages of incorporating a cloud-based system to operate with a plurality of in-vehicle systems, in particular, an ability to maintain cloud storage of user identification data and user blepharometric data for a large number of users, and hence allow that data to "follow" the users between various vehicles over time. For example, a user may have a personal car with a system 101, and subsequently obtain a rental car whilst travelling with its own system 101, and as a result of cloud system 180 the rental car system: has access to the user's historical blepharometric data; is able to perform relationship analysis of the current data collected therein against historical data obtained from the cloud system; and feed into the cloud system the new blepharometric data collected to further enhance the user's historical data store.

Figure 1C:
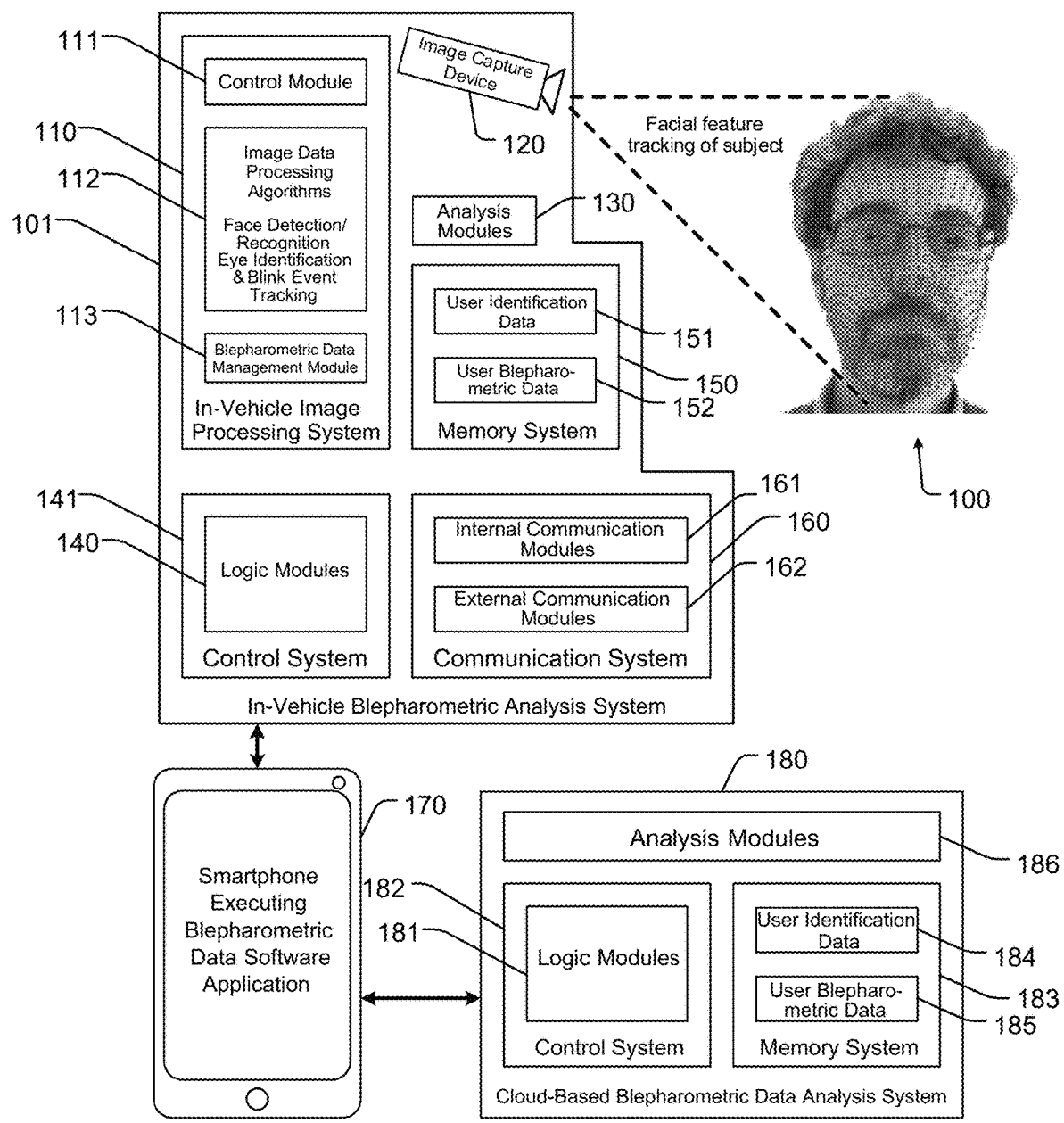
FIG. 1C illustrates an in-vehicle blepharometric data collection/monitoring system according to one embodiment.

FIG. 1C illustrates a further variation where a user has a smartphone 170 that executes a software application configured to communicate with a given local in-vehicle system 101 (for example, via Bluetooth or USB connection) and additionally with cloud system 180 (for example, via a wireless cellular network, Wi-Fi connection, or the like). This provides functionality for communication between system 100 and system 180 without needing to provide Internet connectivity to a vehicle (the in-vehicle system essentially uses smartphone 170 as a network device).

Using a smartphone device as an intermediary between system 101 and system 180 is, in some embodiments, implemented in a matter that provides additional technical benefits. For example:

- In some embodiments, smartphone 170 provides to system 101 data that enabled identification of a unique user, avoiding a need for facial detection and/or other means. For instance, upon coupling a smartphone to an in-car system (which may include system 101 and one or more other in-car systems, such as an entertainment system) via Bluetooth, system 101 receives user identification data from smartphone 170.
- In some embodiments, a most-recent version of a given user's historical blepharometric data (for example, defined as historical baseline values) is stored on smartphone 170, and downloaded to system 101 upon coupling.
- In some embodiments, one or more functionalities of analysis modules 130 are alternately performed via smartphone 170, in which case system 101 optionally is configured to in effect be a blepharometric data collection and communication system without substantive blepharometric data analysis functions (which are instead performed by smartphone 170, and optionally tailored via updating of smartphone app parameters by system 180 for personalised analysis.

The use of smartphone 170 is also in some cases useful in terms of allowing users to retain individual control over their blepharometric data, with blepharometric data not being stored by an in-vehicle system in preference to being stored on the user's smartphone.

Figure 1D:
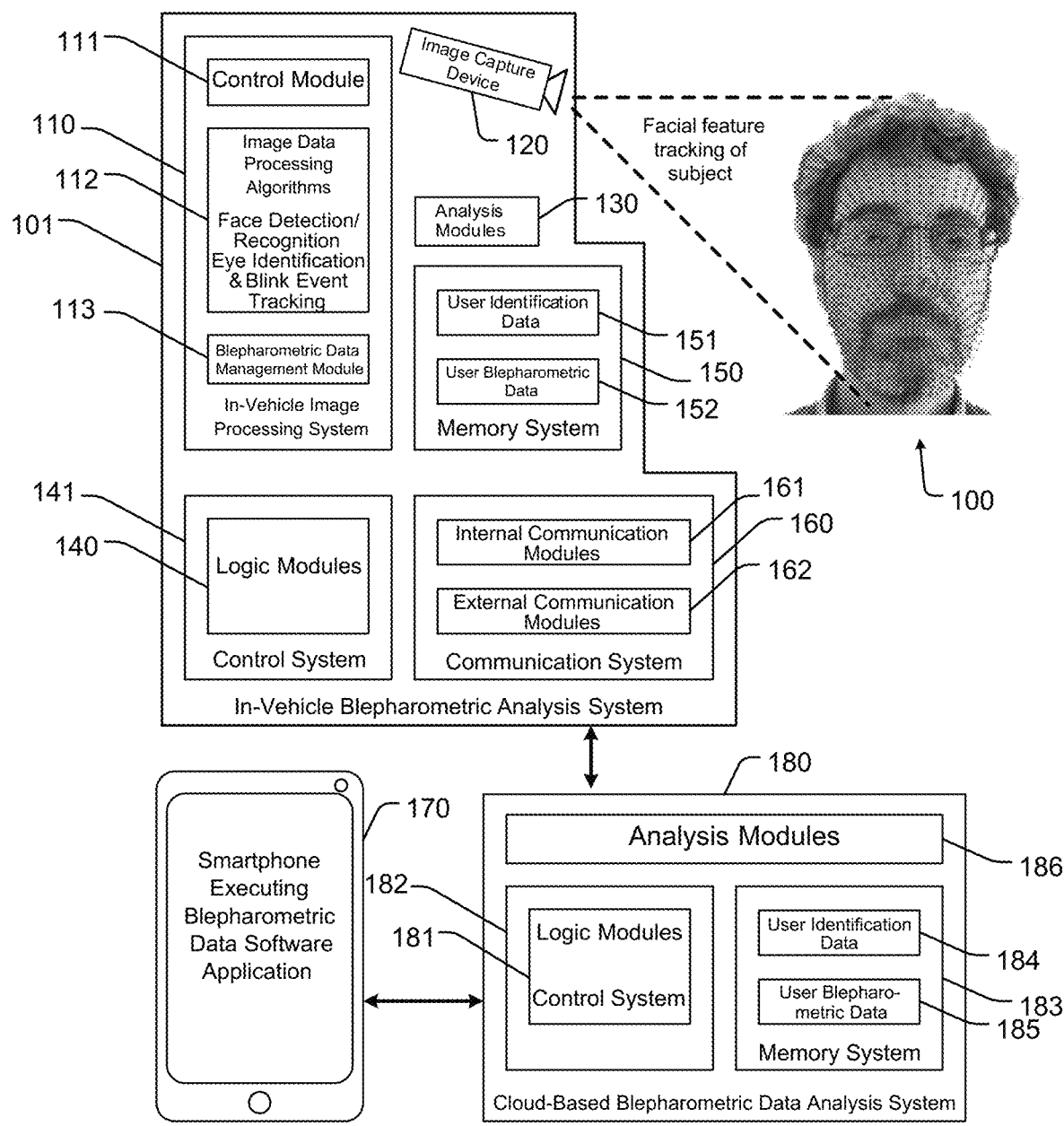
FIG. 1D illustrates an in-vehicle blepharometric data collection/monitoring system according to one embodiment.

FIG. 1D illustrates a further variation in which communication between a local system 101 and cloud system 180 operates in a similar manner to FIG. 1B, but where a smartphone 170 is still present. In such arrangements, the smartphone is optionally used as an output device for information derived from blepharometric data analysis, and/or as a device to confirm identify and approval for blepharometric data collection. For example, in one embodiment a given system 101 identifies a user by way of biometric information (e.g., facial detection) using user identification data stored in memory system 183 of cloud system 180, and a message is sent to smartphone 170 allowing the user to confirm that they are indeed in the location of the relevant system (e.g., smartphone 170), and providing an option to consent to blepharometric data monitoring.

Additional Mass-Transit Functions

A system such as that of FIG. 1A is also able to be integrated into other local systems thereby to provide control instructions to those systems in response to artefacts identified in blepharometric data. An example is provided in FIG. 4, wherein an aircraft 400 an in-vehicle blepharometric data analysis system, which is fed data from image capture devices including devices installed in seat-backs (for example, in a common housing to a seat-back display screen). System 401 is configured to feed data thereby to effect control instructions into an entertainment system 402 and a passenger health/comfort analysis system 403.

In this example, each image capture device is provided in conjunction with a display screen that is configured to deliver audio-visual entertainment (for instance, as is common in aeroplanes), monitoring of subject blepharometric data may be used to provide an enhanced experience with respect to audio-visual data. This may include, for example:

- Decreasing screen brightness and/or volume in response to detection of drowsiness and/or commencement of sleep.
- Deactivation of a screen in response to threshold drowsiness and/or sleep (preferably in combination with pausing of a media file for later resumption of playback).
- Transition of an audio playback track to a sleep/relaxation-inducing track in response to threshold drowsiness and/or sleep (preferably in combination with pausing of a previously in-playback media file for later resumption of playback).
- Delivery of feedback to a multiple passenger monitoring system thereby to facilitate delivery of passenger health and/or comfort monitoring and management based on identifications made from monitoring of blepharometric data.

It will be appreciated that provision of a system that enables collection and analysis of blepharometric data from multiple passengers in a mass-transit vehicle may have additional far-reaching advantages in terms of optimising passenger health and/or comfort during transportation.

In mass-transport embodiments, there is preferably a clear distinction between personalising heath data, which is maintained with privacy on behalf of the user, and non-personalising statistical data, which may be shared with other systems/people. For instance, an individual's neurological conditions are not made available to airline personnel; however, data representative of drowsiness/alertness statistics in a cabin are made available to airline personnel.

Example Cloud-Based Extended Blepharometric Data Monitoring Framework

Figure 2:
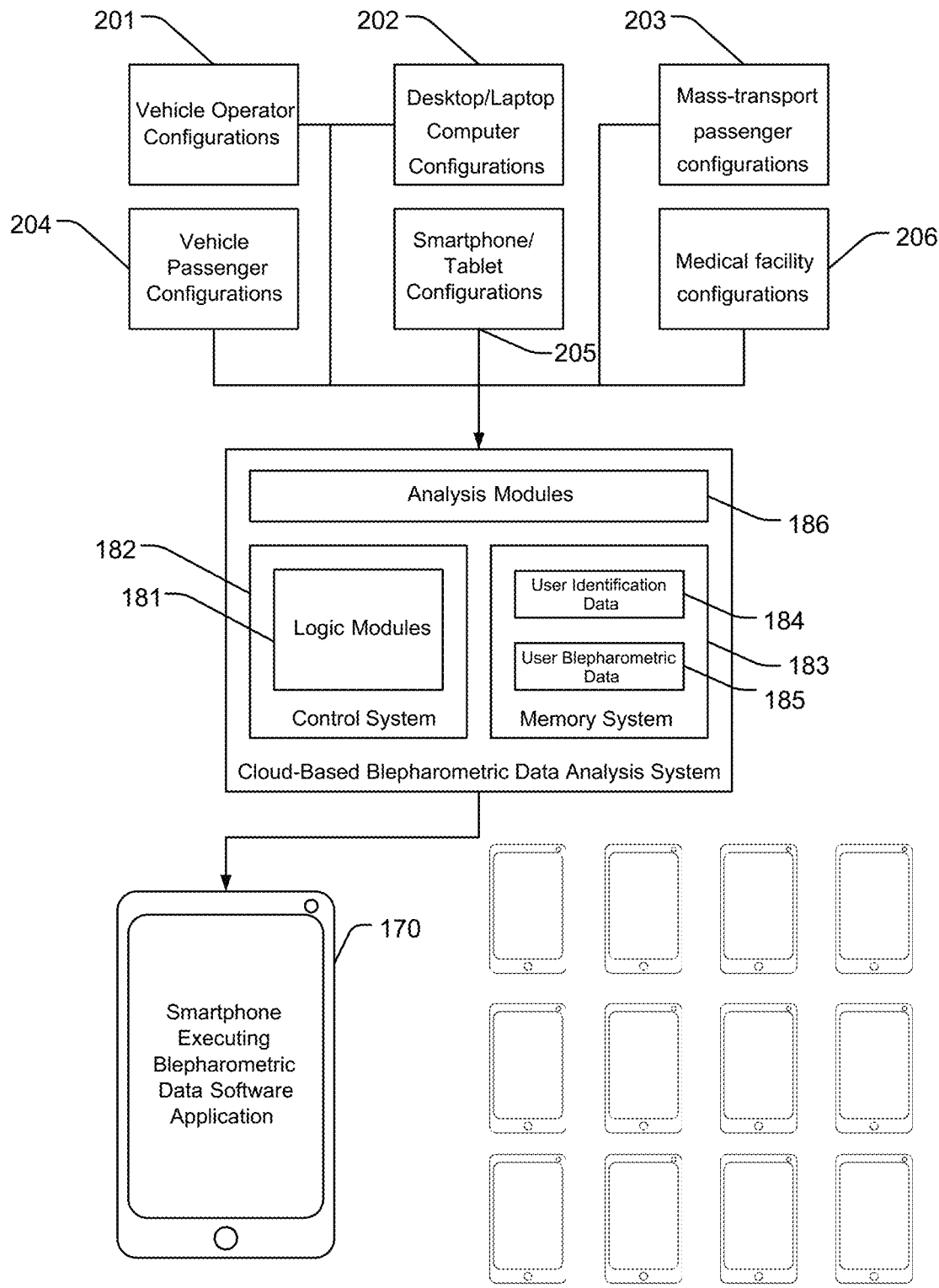
FIG. 2 illustrates a blepharometric data monitoring framework according to one embodiment.

FIG. 2 illustrates an exemplary framework under which a cloud-based blepharometric data analysis system 180 operates in conjunction with a plurality of disparate blepharometric data monitoring systems 201-206. Each of these systems is in communication with system 180, such that user data (for example, user blepharometric data comprising historical data) is able to be utilised for analysis even where a user's blepharometric data is collected from physically distinct monitoring systems. Analysis of blepharometric data (for example, determination of relationships between current and historical data) may be performed at the cloud system 180, at the local systems 201-206, or combined across the cloud and local systems.

Figure 4:
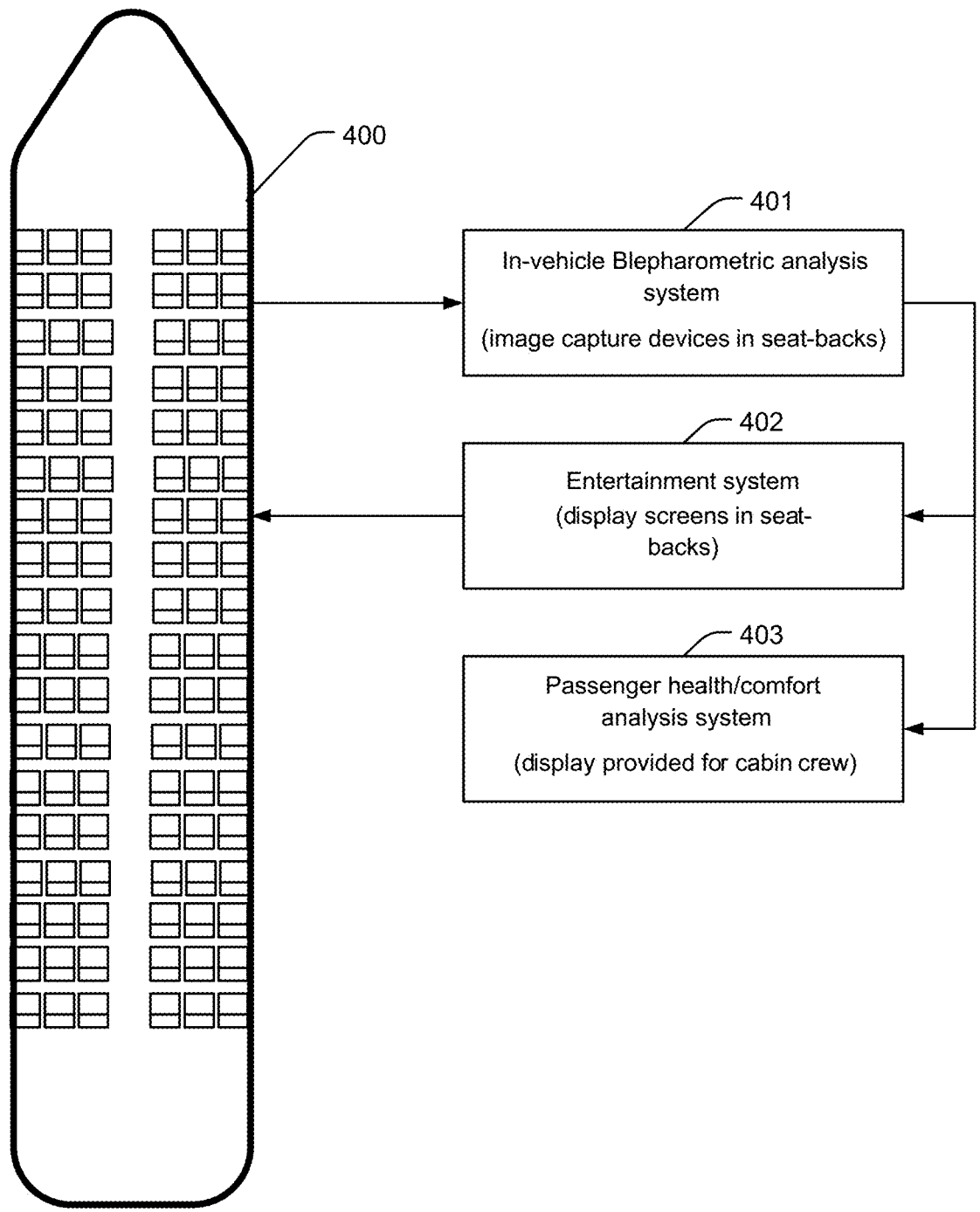
FIG. 4 illustrates a blepharometric data collection/monitoring system in a passenger airplane.

The local systems illustrated in FIG. 2 are:

- Vehicle operator configurations 201. These are in-vehicle systems, such as that of FIG. 1A-1D, in which the image capture device is positioned to capture blepharometric data for an operator of the vehicle.
- Desktop/laptop computer configurations 202. In these configurations, a webcam or other image capture device is used to monitor user blepharometric data, with image-based eyelid movement detection as discussed herein. This may occur subject to: (i) a foreground application (for example, an application, which instructs a user to perform a defined task during which blepharometric data is collected); and/or (ii) a background application, which collects blepharometric data whilst a user engages in other activities on the computer (for example word processing and/or internet browsing).
- Mass transport passenger configurations 203, for example, airlines as illustrated in FIG. 4, busses, trains and the like. Ideally, these are configured such that an image capture device operates in conjunction with a display screen, such that blepharometric data is collected concurrently with the user observing content displayed via the display screen.
- Vehicle passenger configurations 204. These are in-vehicle systems, such as that of FIG. 1A-1D, in which the image capture device is positioned to capture blepharometric data for a passenger of the vehicle. For back-seat applications, these are optionally configured such that an image capture device operates in conjunction with a display screen, such that blepharometric data is collected concurrently with the user observing content displayed via the display screen. For front-seat applications, the camera is positioned based on a presumption that a front seat passenger will for a substantial proportion of the time pay attention to the direction of vehicle travel (e.g., watch the road).
- Smartphone/tablet configurations 206. In these configurations, a front facing camera is used to monitor user blepharometric data, with image-based eyelid movement detection as discussed herein. This may occur subject to: (i) a foreground application (for example, an application, which instructs a user to perform a defined task during which blepharometric data is collected); and/or (ii) a background application, which collects blepharometric data whilst a user engages in other activities on the computer (for example, messaging and/or social media application usage).
- Medical facility configurations 206. These may make use of image processing-based blepharometric data monitoring, and/or other means of data collection (such as infrared reflectance oculography spectacles). These provide a highly valuable component in the overall framework: due to centralised collection of blepharometric data over time for a given subject from multiple locations over an extended period of time, a hospital is able to perform point-in-time blepharometric data collection and immediately reference that against historical data thereby to enable identification of irregularities in neurological conditions.

FIG. 2 also shows how system 180 is able to interact with a plurality of user mobile devices such as device 170. User identification data 184 provides addressing information thereby to enable system 180 to deliver messages, alerts, and the like to correct user devices.

Beyond advantages of providing an ability to carry user blepharometric data baselines and data collection between physical collection systems, and added benefit of a system such as that of FIG. 2 is an ability to personalize condition prediction algorithms for individual users. This is achieved by: (i) identifying a personalized blepharometric data biomarker for a given user, wherein that blepharometric data artefact is representative of a particular neurological condition; and (ii) configuring the system such that whenever that particular user is identified, an analysis system executes a process configured to monitor for that biomarker (and perform a defined action in response). For example, in one example it is determined that a particular person displays a specific blepharometric data biomarker (for example, threshold spiking in negative inter event duration) in the lead-up to a seizure event; a process configured to monitor for that biomarker is initialized in response to identification of that person. For example, an analysis module of an in-vehicle device is configured for such monitoring once the person is detected, and provides a seizure warning when the biomarker is detected.

Example Blepharometric Data Relationship Analysis System

Figure 5:
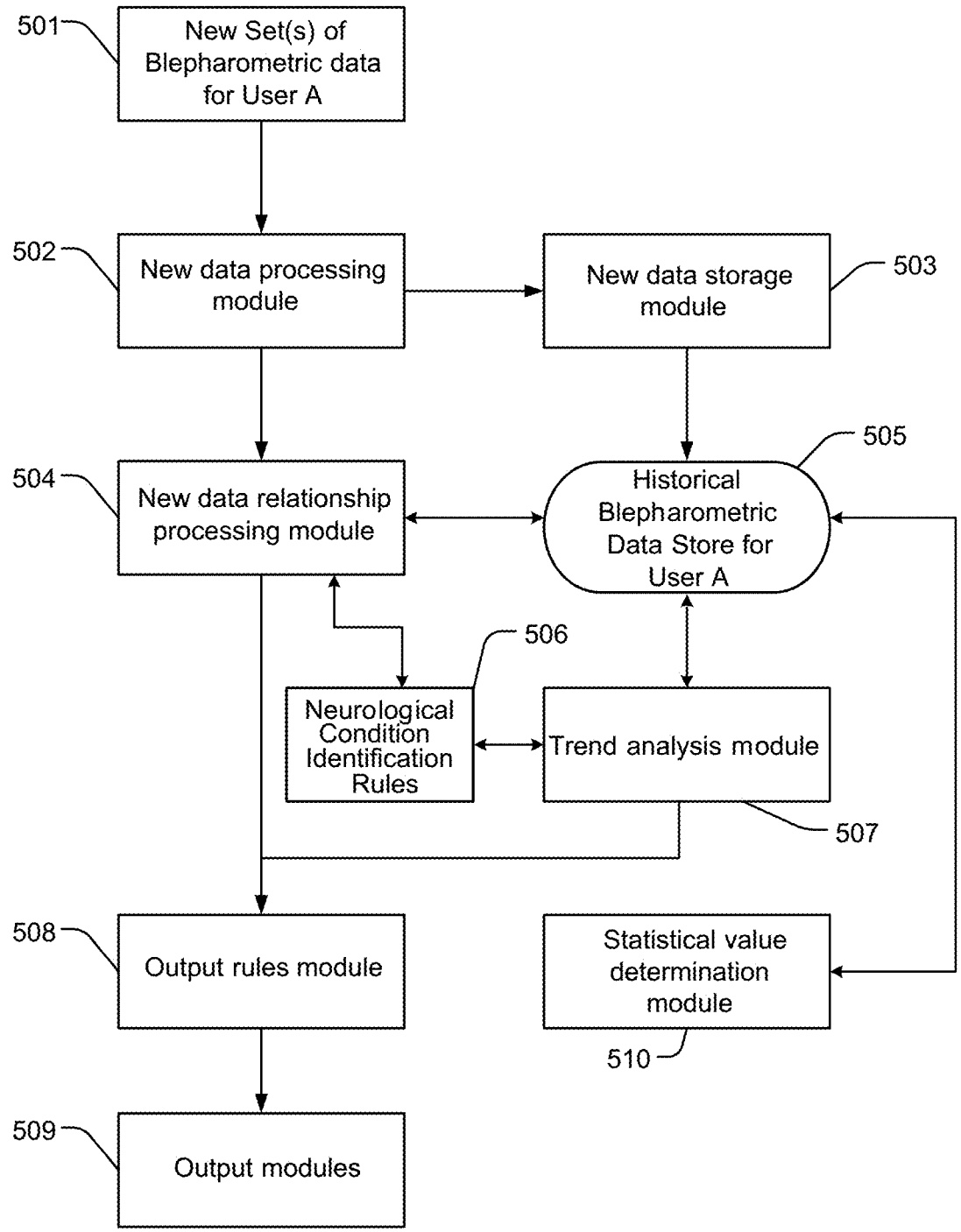
FIG. 5 illustrates an analysis system according to one embodiment.

FIG. 5 illustrates an example blepharometric data relationship analysis system, which may be incorporated into embodiments described above. In some cases, components/functionalities of this system are distributed across local and cloud-based processing systems.

One or more new sets of blepharometric data 501, which may be defined via any collection system, for instance, as shown in FIG. 2, are received by a new data processing module 502. Module 502 is configured to perform data validation and/or data cleaning, thereby to ensure that the data is suitable for analysis and/or storage. For example, data displaying irregularities and/or having a sample time below a given threshold is excluded. A new data storage module 503 is configured to coordinate storage of the new set or sets of data 501, following processing module 502, into a data store 505 containing historical blepharometric data for the user.

A statistical value determination module 510 applies an expandable set of processing algorithms to data in store 505 thereby to extract a range of statistical values (for example, averages for blepharometric data artefacts, optionally categorized based on collection conditions and other factors). These statistical values are stored in data store 505 thereby to maintain richer detail regarding baseline blepharometric data values for the user, preferably in a way that is tied to defined relationship analysis algorithms. That is, if an algorithm X to determine a condition Y relies on analysis of a blepharometric data artefact Z, then module 510 is preferably configured to apply an algorithm configured to extract artefact Z from user blepharometric data.

A new data relationship processing module 504 is configured to identify relationships between new data 501 and historical data store 505. Data rules to facilitate the identification of particular relationships that are known to be representative (or predictively representative) of neurological conditions are defined in condition identification rules 506. Rules 506 are periodically updated based on new knowledge regarding blepharometric data/neurological condition research. For example, a given rule defines a category of relationship between one or more blepharometric data artefacts in new data 501 and one or more baseline values extracted from historical data in store 505 based on operation of module 510.

In the case that a defined category of relationship is identified by module 504, representative data is passed to an output rules module 508, which contains logical rules that define how a user is to be notified (e.g., in-vehicle alert, message to smartphone app, or email), and in response a given output module 509 is invoked to provide the designated output.

A trend analysis module 507 is configured to continuously, periodically or in an event driven manner (for example, in response to receipt of new blepharometric data) identify trends/changes in user blepharometric data. Again, data rules to facilitate the identification of particular trends that are known to be representative (or predictively representative) of neurological conditions are defined in condition identification rules 506. Rules 506 are periodically updated based on new knowledge regarding blepharometric data/neurological condition research. For example, a given rule defines a threshold deviation in one or more artefacts over a threshold time as being predictively representative of a neurological condition.

Again, the case that a defined category of relationship is identified by module 507, representative data is passed to an output rules module, which contains logical rules that define how a user is to be notified (e.g., in-vehicle alert, message to smartphone app, or email), and in response a given output module 509 is invoked to provide the designated output.

It will be appreciated that, in this manner, the system of FIG. 5 is configurable to monitor for a range of neurological conditions that are identifiable in blepharometric data based on point-in-time variations from known baselines that are generated and refined over extended period (i.e., based on a collection of time-separated data sets), and trends in blepharometric data over time (even where differences between consecutive data sets are relatively minor).

It will be appreciated that this form of data collection and analysis is of significant use in the context of predicting and understanding neurological conditions, for example, in terms of: (i) identifying potential degenerative conditions and rates of onset; (ii) identifying point-in-time events that led to sudden changes in neurological conditions; (iii) monitoring long-term effects of contact sports (e.g., concussive brain injuries) for participants, (iv) personalizing blepharometric data analysis for individual users.

Physiological Event Prediction Technology

Some embodiments provide methods and associated technology that enables retrospective analysis of blepharometric data driving subsequent hardware/software configuration, thereby to provide for personalized and/or generalized biomarker identification, and from this enable automated predictions of physiological events or conditions.

As used herein, the phrase "physiological event or condition" is used to broadly describe a range of observable human states, including states that are generally identifiable by a particular point in time change (for example, a seizure, onset of a medical condition, and so on, which are able to be classed as "events"), and states that are experienced over a longer period of time (for example, drowsiness, the presence of a particular disease or ailment, a stage of consciousness, a level of physical and/or cognitive performance, and so on, which are able to classed as "conditions"). In this regard, the phrase "physiological event or condition" is intended to be afforded a broad interpretation, so as not to necessarily limit human characteristics that may be predicted based on analysis of blepharometric data as discussed herein.

According to one embodiment, a method includes receiving input representative of an observed occurrence of a physiological event or condition. This input is, by way of example, defined by an identifier that is represented of the physiological event or condition, and time data (for example, a time stamp, or time range) associated with the observance. The input may be derived from a range of sources, including:

Medical devices, for example, electrocardiogram (EEG), electroencephalogram (ECG), heart rate monitors, and so on.

Pathology results (for example, derived from blood and/or urine samples).

Interactive test results, for example, performance in a predefined test administer by a testing computer software module.

Human subjective observations, inputted, for example, via a smartphone app or the like, optionally in response to a prompt.

Environmental sensors that monitor an area in which a human subject is contained.

It will be appreciated that these are examples only.

The method then includes identifying a set of baseline blepharometric data artefacts data for the subject. The baseline blepharometric data artefacts are preferably collected via blepharometric data monitoring hardware and associated processing software over an extended period of time, and are optionally associated with states of activity. For example, in one embodiment a user may have separate sets of baseline blepharometric data artefacts data for states including one or more of: sedentary; operating machinery; operating an automobile; mild physical activity; and vigorous physical activity. In some embodiments, allowances are made of environmental conditions including ambient light, wind, temperature and/or humidity. This assists in refining baseline artefact data in a manner that accounts for major influencing factors.

The baseline blepharometric data artefacts data is optionally defined based on statistical ranges for observation of blepharometric data artefacts determined to be "normal" for the human subject (either the subject as a specific individual, or the subject as abstracted from demographic and/or other identifying characteristics). The blepharometric data artefacts preferably include one or more of the following:

Measurements defined by, or representative of statistical attributes of, blink total duration (BTD);

Measurements defined by, or representative of statistical attributes of, inter-event duration (IED);

Measurements defined by, or representative of statistical attributes of, blink amplitudes;

Measurements defined by, or representative of statistical attributes of, eyelid velocities;

Measurements defined by, or representative of statistical attributes of, amplitude to velocity ratios for blink events;

Measurements defined by, or representative of statistical attributes of, negative inter-event duration (negative IED);

Blink event counts, including blink event counts for a set of blink events having defined attributes occurring within a defined time period;

Measurements defined by, or representative of statistical attributes of, blink eye closure duration (BECD); and Measurements defined by, or representative of statistical attributes of, duration of ocular quiescence (DOQ).

In some embodiments, blepharometric data artefacts include artefacts derived from a range of signal processing techniques, for example, Fourier transforms, wavelets, discrete cosine transformations and the like, thereby to extract blepharometric data artefacts that are representative of a blepharometric data signal as opposed to direct measurements of blink features. That is, blepharometric data representative of eyelid position over time may be treated as a waveform for the purposes of analysis and artefact extraction.

It will be appreciated that the term "blepharometric data artefacts" as used elsewhere in this specification may refer to any one or more of the above artefacts. The baseline blepharometric data artefacts and other blepharometric data artefacts used for this method are optionally collected and managed via systems as described further above.

The method additionally includes extracting a set of event blepharometric data artefacts for the subject for a period preceding and/or including the observed occurrence of a physiological event or condition. For example, this data may be obtained via blepharometric data collection means described above, including (but not limited to):

wearable configurations including infrared reflectance oculography components;

vehicle operator configurations, in which an image capture device is positioned to capture blepharometric data for an operator of the vehicle;

desktop/laptop computer configurations in which a webcam or other image capture device is used to monitor subject blepharometric data subject to: (i) a foreground software application; and/or (ii) a background software application which collects blepharometric data whilst a subject engages in other activities on the computer;

mass transport passenger configurations in which an image capture device operates in conjunction with a display screen, such that blepharometric data is collected concurrently with the subject observing content displayed via the display screen;

vehicle passenger configurations in which an image capture device is positioned to capture blepharometric data for a passenger of the vehicle;

smartphone/tablet configurations in which a front facing camera is used to monitor subject blepharometric data, subject to: (i) a foreground application; and/or (ii) a background application, which collects blepharometric data whilst a subject engages in other activities on the smartphone/tablet;

other monitor-based configurations wherein a camera or other device is used to monitor subject blepharometric data, for example, whilst the subject watches a television show or plays video games; and medical facility configurations.

The step of extracting a set of event blepharometric data artefacts for the subject for a period preceding and/or including the observed occurrence of the physiological event or condition optionally includes: identifying a timestamp associated with the physiological event or condition; identifying a set of blepharometric data for the subject stored in a database having timestamps for a predefined period preceding and/or including the observed occurrence of the physiological event or condition; and extracting that blepharometric data for from the database. It will be appreciated that the input representative of an observed occurrence of a physiological event or condition is not necessarily received in real time, and in some embodiments, this data is received at a later stage hence necessitating identification and extraction of stored data.

A computer program is configured to compare the baseline blepharometric data artefacts with the event blepharometric data artefacts, thereby to identify one or more "anomaly artefacts." An anomaly artefact is an artefact observed in the event blepharometric data artefacts that is outside of a statistical range associated with a corresponding artefact defined by the baseline blepharometric data artefacts, or a combination of one or more event blepharometric data artefacts that is outside of a statistical range associated with a corresponding combination of artefacts defined by the baseline blepharometric data artefacts. For example, this might be an increase in IED spiking, a prolonged decrease in BTD, and so on. Preferably the computer program is configured to autonomously define a substantial number of these anomaly artefacts, for example, using combinations and permutations of observed anomalies. These are then subjected to an anomaly artefact analysis process thereby to selectively define a candidate blepharometric data indicator for the subject. For example, the anomaly artefact analysis process may include one or more of the following:
- Determination whether a given anomaly artefact has a threshold probability of being associated with a known form of physiological event or condition other than the observed physiological event or condition. For example, a database may associate a series of anomaly artefacts with known common physiological events or conditions, which cause expected variations from baselined.
- Determination whether a given anomaly artefact has been observed as a candidate blepharometric data indicator for one or more other subjects in respect of a corresponding observed physiological event or condition.
- Determination whether a given anomaly artefact has been previously observed for the same human subject in respect of another observed physiological event or condition.
- Other predefined filtering algorithms.

It will be appreciated that this anomaly artefact analysis process optionally is performed thereby to provide a filtering of a set of identified anomaly artefacts thereby to identify a reduced subset that have highest probability of in causational association with the observed physiological event or condition.

Once a candidate blepharometric data indicator has been identified, that indicator is preferably subjected to a testing phase. This testing phase may include, in response to future identification of the candidate blepharometric data indicator, determining presence/onset of the associated physiological event or condition. That is, the candidate blepharometric data indicator is tested to determine whether it provides a repeatable predictor for the associated physiological event or condition. This may include testing for the specific subject for which the indicator was defined, and/or a wider range of subjects (for example, subjects having corresponding characteristics and/or attributes). A set of rules are defined thereby to score candidate indicators, with candidates scoring below a threshold level being discarded. This may include scoring as a personalized indicator (i.e., for a single human subject) and/or a global indicator (i.e., for a plurality of human subjects, such as a class of human subjects having defined attributes).

In some embodiments, the testing phase makes use of a smartphone app, which prompts a subject to input, at a defined time relative to observation of a candidate indicator, data representative of personal observance of a specified physiological event or condition (i.e., the associated physiological event or condition for that indicator). This is preferably retrospective; for example, a prompt "did you recently experience a seizure" or the like. It will be appreciated that other means including human condition monitoring equipment may be used thereby to obtain objective measurements.

Following a testing phase, one or more candidate indicators may be identified as predictive indicators for particular physiological event or condition, optionally limited to specific individual subjects and/or classes of subjects, and/or subjects in specified states of human activity. It will be appreciated that learning algorithms and the like are able to be employed to assist in this process.

Figure 6:
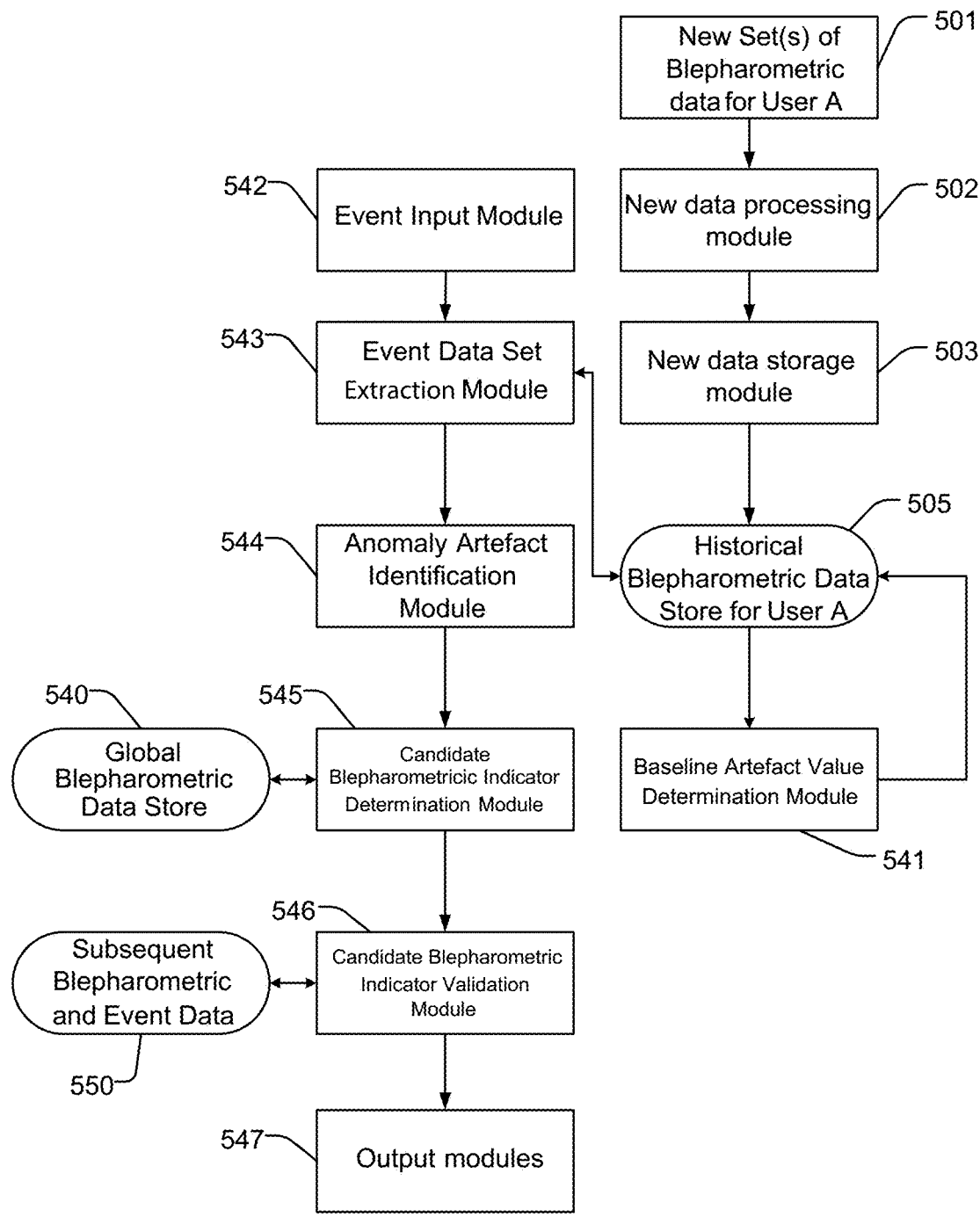
FIG. 6 illustrates a method according to one embodiment.

FIG. 6 illustrates a further example embodiment. Block 501 represents input of a new one or more sets of blepharometric data for a user User A. The new data is cleaned block 502) and processed for storage (block 503) in a data store 505. A baseline artefact value determination module 541 operates to maintain baseline blepharometric data for User A.

An event input module 542 is used to enable inputting of timestamped event data represented of an observed physiological event or condition. Data is extracted from store 505 by a module 543, thereby to obtain blepharometric data temporally relevant to the event. This data is processed by an anomaly artefact identification module 544, and passed to a candidate blepharometric data indicator determination module 545. Module 545 processes that data against a global blepharometric data store and optionally one or more other sources thereby to defined one or more candidate blepharometric data indicators for the observed physiological event or condition. These are then processed by a validation module 546, which accesses one or more sources of subsequent blepharometric and event data 550 (which may include data provided by stores 505 and/or 509) thereby to test the candidate indicator(s). In the case of successful validation, an output module 547 is configured to output the indicators (for example, enabling the indicator to be accessed by a blepharometric data monitoring device thereby to, in real time, provide data about predicted current and/or anticipated physiological events or conditions for a subject from which blepharometric data is being collected.

Figure 7:
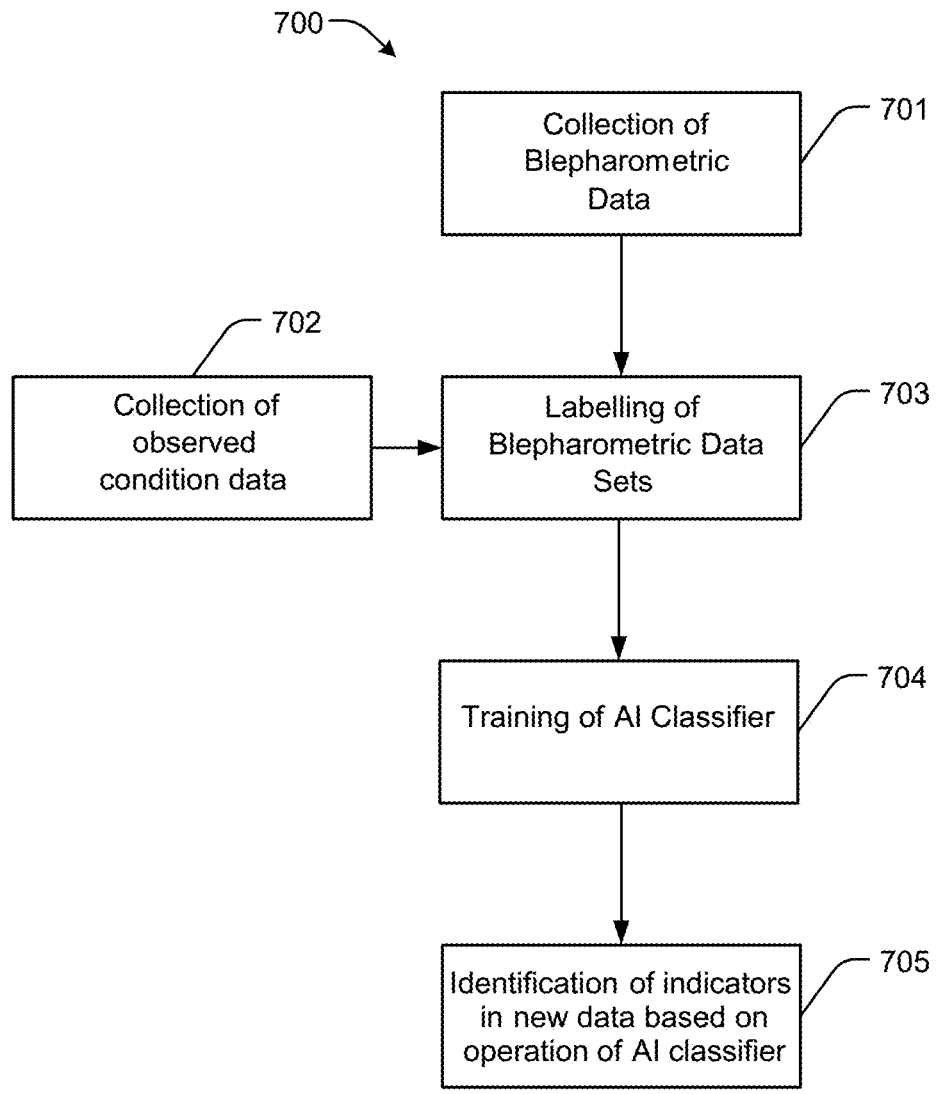
FIG. 7 illustrates a method according to one embodiment.

A further embodiment makes use of an AI classifier (for example, a neural network) thereby to assist in identification of candidate blepharometric data indicators. This is described below by reference to method 700 of FIG. 7.

Block 701 represents collection of blepharometric data from a plurality of subjects, for example, using one or more of the various data collection techniques described above. This data is associated with attributes of the subjects, for example, the subject's identify (for example, based on a depersonalizing unique identifier), demographic information (for example, age, gender, and the like), and optional medical record information (for example, known medical conditions).

Block 702 represents collection of observed condition data. For example, this may include receiving input representative of an observed occurrence of a prescribed physiological event or condition as described above. This may additionally include other observed condition data, for example:
- Activity data, for example, as determined via wearable devices containing IMU/accelerometer modules, GPS modules, heart rate monitors, and the like. This activity data is preferably processed thereby to determine a subject's current state of activity, for example: "light exercise," "heavy exercise," "sedentary," "driving" and the like. It will be appreciated that there are existing technologies, which allow determination of such activity states from wearable devices, for example, smartwatches containing IMUS. Activity may also be inferred from the relevant blepharonic data collection system (for example, an in-vehicle system monitoring a driver infers that the subject is driving).
- External conditions data, for example, based on an ambient light meter carried by a smartwatch, microphone carried by a smartwatch, and so on.
- Data indicating absence of occurrence of any of the prescribed physiological events or conditions. This assists in identification of baseline data.

Block 703 represents labelling of blepharometric data sets. Each data set includes blepharonic data describing subject eyelid position as a function of time, and labelled metadata including, for example, information regarding the subject, activity data, external conditions data, and data regarding observance/non-observance of occurrence of physiological conditions. A plurality of data sets are preferably defined a given stream of data collected from a subject, for example:

A data set is defined for a one or more periods (for example, a 5 minute period, 10 minute period, and 1-hour period) leading up to an observed occurrence of a physiological event or condition.

A data set is defined for a period of a common state of activity and/or external conditions in absence of observance of an observed occurrence of a physiological event or condition.

Block 704 represents training of an AI classifier, by feeding to the classifier the labelled blepharometric data sets. This is used to train the classifier to predict either: (i) low likelihood of onset of any of a set of prescribed physiological conditions; or (ii) threshold likelihood of onset of one or more of a set of prescribed physiological conditions. In some embodiments, a scoring/percentage based approach is used thereby to show a likelihood of occurrence of a given one of the prescribed physiological conditions (for example, to enable a graduated/risk-based alert system).

Block 705 represents operating the AI classifier to analyze partially labelled data blepharometric data sets. These data sets are defined in real-time based on collection of blepharometric data from a user, and partially labelled (in accordance with the same schema as the training data, which is provided to the classifier at 704) with attributes of the subject, and preferably activity data and/or external conditions data. It will be appreciated that these data sets are not labelled to indicate presence/absence of the occurrence the prescribed physiological events or conditions, and the classifier operates to predict a likelihood of a current or future occurrence of each of the prescribed physiological events or conditions.

Such an approach is useful in allowing for analysis of a wider range of data attributes beyond a predefined set of blepharonic artefacts, given enhance pattern identification and matching abilities of AI based classifiers.

CONCLUSIONS AND INTERPRETATION

It will be appreciated that the above disclosure provides analytic methods and associated technology that enables improved analysis of human neurological conditions.

It should be appreciated that in the above description of exemplary embodiments of the present disclosure, various features of the present disclosure are sometimes grouped together in a single embodiment, FIG., or description thereof for the purpose of streamlining the disclosure and aiding in the understanding of one or more of the various inventive aspects. This method of disclosure; however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the present disclosure, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the present disclosure.

In the description provided herein, numerous specific details are set forth. However, it is understood that embodiments of the present disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the present disclosure, those skilled in the art will recognize that other and further modifications may be made thereto without departing from the spirit of the present disclosure, and it is intended to claim all such changes and modifications as falling within the scope of the claimed invention. For example, any formulas given above are merely representative of procedures that may be used. Functionality may be added or deleted from the block diagrams and operations may be interchanged among functional blocks. Steps may be added or deleted to methods described within the scope of the present disclosure.

The invention claimed is:

1. A method for processing blepharometric data for a subject, the method including:
   (i) receiving a set of blepharometric data for the subject;
   (ii) receiving input representative of an observed occurrence of a physiological event or condition;
   (iii) defining one or more blepharometric data sets based on the blepharometric data, wherein each data set is labelled with data representative of presence/absence of an observed occurrence of a physiological event or condition thereby to define labelled training data; and
   (iv) training an AI classifier based on the labelled training data;
   such that the AI classifier is configured thereby to predict presence/absence of a current or future occurrence of a physiological event or condition based on a new set of blepharometric data, wherein that new set of blepharometric data is not labelled with data representative of presence/absence of an observed occurrence of a physiological event or condition;

wherein the step of defining one or more blepharometric data sets based on the blepharometric data includes processing data representative of the subject's eyelid position as a function of time thereby to:
(i) identify a plurality of events, wherein each event is defined by a set of time blepharometric data for a positive or negative change in eyelid amplitude that is greater than a given velocity threshold for a given time duration;
(ii) identify a plurality of individual blinks, wherein each individual blink is a pairing of an event corresponding to a positive change in amplitude position and a negative change in amplitude position that are within predefined relative amplitude and position limits; and
(iii) processing data representative of the identified events and the identified individual blinks thereby to define data artifacts which are blepharometric data sets, the data artifacts including:
   A. one or more data artifacts representative of statistical attributes of inter-event timings; and
   B. one or more artifacts representative of statistical attributes individual for blink events including velocity.

2. A method according to claim 1 wherein the input representative of an observed occurrence of a physiological event or condition includes timestamped data representative of an event or condition identified by a separate monitoring system.

3. A method according to claim 2 wherein the separate monitoring system includes a brain activity monitoring system.

4. A method according to claim 2 wherein the separate monitoring system includes a cardiovascular activity monitoring system.

5. A method according to claim 2 wherein the separate monitoring system includes a monitoring system that receives results from an interactive test.

6. A method according to claim 1 wherein the input representative of an observed occurrence of a physiological event or condition includes timestamped data representative of an event or condition identified manually and inputted via in input interface.

7. A method according to claim 1 wherein step (iii) includes caballing each data set with activity data representative of a current state of activity for the subject when the blepharometric data was obtained.

8. A method according to claim 7 wherein the activity data is derived from processing of accelerometer/IMU data from a wearable device worn by the subject.

9. A method according to claim 7 wherein the activity data is derived from processing of biometric data from a biometric monitoring device worn by the subject.

10. A method according to claim 1 wherein the blepharometric data is derived from one or more of the following sources:

wearable configurations including infrared reflectance oculography components;

vehicle operator configurations, in which an image capture device is positioned to capture blepharometric data for an operator of the vehicle;

desktop/laptop computer configurations in which a webcam or other image capture device is used to monitor subject blepharometric data subject to: (i) a foreground software application; and/or (ii) a background software application, which collects blepharometric data whilst a subject engages in other activities on the computer;

mass transport passenger configurations in which an image capture device operates in conjunction with a display screen, such that blepharometric data is collected concurrently with the subject observing content displayed via the display screen;

vehicle passenger configurations in which an image capture device is positioned to capture blepharometric data for a passenger of the vehicle;

smartphone/tablet configurations in which a front facing camera is used to monitor subject blepharometric data, subject to: (i) a foreground application; and/or (ii) a background application, which collects blepharometric data whilst a subject engages in other activities on the smartphone/tablet; and medical facility configurations.

11. A method according to claim 1, wherein the one or more data artifacts representative of statistical attributes of inter-event timings include a data artifact representative of duration of ocular quiescence.

12. A method according to claim 1, wherein the one or more data artifacts representative of statistical attributes of inter-event timings include a data artifact representative of blink eye closure duration.

13. A method according to claim 1 wherein the one or more data artifacts representative of statistical attributes of inter-event timings include a data artifact representative of a time period between blink events.

14. A method according to claim 13, wherein the time period between blink events is measured between blink initiation times for consecutive individual blinks.

* * * * *

UNITED STATES PATENT AND TRADEMARK OFFICE
CERTIFICATE OF CORRECTION

PATENT NO. : 12,159,241 B2
APPLICATION NO. : 17/288336
DATED : December 3, 2024
INVENTOR(S) : Scott Coles and Trefor Morgan It is certified that error appears in the above-identified patent and that said Letters Patent is hereby corrected as shown below:

In the Specification

| | | |
|---|---|---|
| Column 1, | Lines 34-35, | change "personalised and/or" to --personalized and/or-- |
| Column 1, | Line 35, | change "and/or generalised biomarker" to --and/or generalized biomarker-- |
| Column 2, | Lines 52-53, | change "data whilst a subject" to --data while a subject-- |
| Column 2, | Line 66, | change "data whilst a subject" to --data while a subject-- |
| Column 3, | Lines 49-50, | change "data artefacts" to --data artefacts.-- |
| Column 3, | Lines 57-58, | change "A method according to any preceding claim wherein performing" to --In some embodiments, performing-- |
| Column 3, | Lines 64-65, | change "A method according to any preceding claim wherein performing" to --In some embodiments, performing-- |
| Column 4, | Lines 5-6, | change "A method according to any preceding claim wherein the set" to --In some embodiments, the set-- |
| Column 4, | Lines 10-11, | change "A method according to any preceding claim wherein the set" to --In some embodiments, the set-- |
| Column 4, | Lines 15-16, | change "A system according to any preceding claim including configuring" to --In some embodiments, the method further includes configuring-- |
| Column 4, | Line 52, | change "the terms comprising, comprised of or which comprises is an" to --the terms "comprising," "comprised of" or "which comprises" is an-- |
| Column 4, | Lines 54-55, | change "the term comprising, when used" to --the term "comprising," when used-- |
| Column 4, | Lines 59-60, | change "terms including or which includes or that |

Signed and Sealed this
Eleventh Day of February, 2025

Coke Morgan Stewart
*Acting Director of the United States Patent and Trademark Office*

| | | |
|---|---|---|
| | | includes as used" to --terms "including" or "which includes" or "that includes" as used-- |
| Column 4, | Lines 63-64, | change "and means comprising." to --and means "comprising."-- |
| Column 5, | Line 40, | change "subject's behavioural state" to --subject's behavioral state-- |
| Column 5, | Line 45, | change "subject's behavioural state," to --subject's behavioral state,-- |
| Column 5, | Line 51 | change "herein is focussed on collection" to --herein is focused on collection-- |
| Column 6, | Line 44, | change "Determination time period" to --Determination of a time period-- |
| Column 7, | Line 21, | change "cars, aeroplanes, trains," to --cars, airplanes, trains,-- |
| Column 7, | Line 23, | change "allows long term blepharometric" to --allows long-term blepharometric-- |
| Column 7, | Line 24, | change "on an individualised basis," to --on an individualized basis,-- |
| Column 7, | Lines 29-30, | change "and personalised detection" to --and personalized detection-- |
| Column 8, | Line 40, | change "some embodiments that is one" to --some embodiments, that is one-- |
| Column 8, | Lines 43-44, | change "Furthermore, whilst embodiments" to --Furthermore, while embodiments-- |
| Column 8, | Line 48, | change "is anonymised such" to --is anonymized such-- |
| Column 8, | Lines 51-52, | change "of aeroplanes and" to --of airplanes and-- |
| Column 8, | Line 64, | change "described herein a camera-based" to --described herein, a camera-based-- |
| Column 8, | Line 65, | change "system utilises image data" to --system utilizes image data-- |
| Column 9, | Line 5, | change "some embodiments an analysis" to --some embodiments, an analysis-- |
| Column 9, | Line 48, | change "some embodiments multiple" to --some embodiments, multiple-- |
| Column 9, | Line 60, | change "for analysing blepharometric" to --for analyzing blepharometric-- |
| Column 10, | Lines 27-28 | change "of short term onsets" to --of short-term onsets-- |
| Column 10, | Lines 29-30, | change "seizures and long term onsets" to --seizures and long-term onsets-- |
| Column 10, | Line 30, | change "example, long term detection" to --example, long-term detection-- |
| Column 10, | Lines 30-31, | change "the short term is" to --the short-term is-- |
| Column 11, | Line 12, | change "system. Whilst it is" to --system. While it |

CERTIFICATE OF CORRECTION (continued)
U.S. Pat. No. 12,159,241 B2

| | | |
|---|---|---|
| | | is-- |
| Column 11, | Line 33, | change "embodiment device" to --embodiment, device-- |
| Column 11, | Line 36, | change "embodiment device" to --embodiment, device-- |
| Column 11, | Lines 38-39, | change "In some embodiments a combination" to --In some embodiments, a combination-- |
| Column 11, | Lines 48-49, | change "such embodiments there are" to --such embodiments, there are-- |
| Column 12, | Line 5, | change "some embodiments the algorithms" to --some embodiments, the algorithms-- |
| Column 12, | Line 6, | change "other embodiments both eye" to --other embodiments, both eye-- |
| Column 12, | Line 9, | change "preferred embodiment this is" to --preferred embodiment, this is-- |
| Column 12, | Lines 38-39, | change "data s collected only" to --data is collected-- |
| Column 12, | Lines 48-49, | change "and analyse blepharometric" to --and analyze blepharometric-- |
| Column 12, | Lines 52-53, | change "collect and analyse blepharometric" to --collect and analyze blepharometric-- |
| Column 12, | Line 67, | change "stored in data 152" to --stored in user blepharometric data 152-- |
| Column 14, | Line 1, | change "system 140 included" to --system 141 included-- |
| Column 14, | Line 1, | change "modules 141, which" to --modules 140, which-- |
| Column 14, | Line 2, | change "system 140. This" to --system 141. This-- |
| Column 14, | Line 4, | change "be provide din response" to --be provided in response-- |
| Column 14, | Line 17, | change "modules 141 are able" to --modules 140 are able-- |
| Column 14, | Line 18, | change "functionalities thereby" to --functionalities, thereby-- |
| Column 14, | Line 31, | change "User-personalised drowsiness" to --User-personalized drowsiness-- |
| Column 14, | Line 36, | change "and/or long term" to --and/or long-term-- |
| Column 14, | Line 39, | change "Personalised prediction" to --Personalized prediction-- |
| Column 14, | Line 43, | change "on individually-verified seizure" to --on individually verified-- |
| Column 15, | Line 8, | change "records are synchronised between" to --records are synchronized between-- |
| Column 15, | Line 13, | change "periodically synchronised with" to --periodically synchronized with-- |
| Column 15, | Lines 14-15, | change "upon an unrecognised user" to --upon an unrecognized user-- |

CERTIFICATE OF CORRECTION (continued)
U.S. Pat. No. 12,159,241 B2

| Column 15, | Line 20, | change "data us uploaded" to --data is uploaded-- |
| Column 15, | Line 66, | change "rental car whilst travelling" to --rental car while travelling-- |
| Column 16, | Line 42, | change "for personalised analysis." to --for personalized analysis.-- |
| Column 16, | Lines 55-56, | change "one embodiment a given" to --one embodiment, a given-- |
| Column 17, | Line 11, | change "in aeroplanes), monitoring" to --in airplanes), monitoring-- |
| Column 17, | Lines 33-34, | change "terms of optimising passenger" to --terms of optimizing passenger-- |
| Column 17, | Line 36, | change "between personalising heath data," to --between personalizing health data,-- |
| Column 17, | Lines 37-38, | change "non-personalising heath data," to --non-personalizing health data,-- |
| Column 17, | Line 51, | change "to be utilised for analysis" to --to be utilized for analysis-- |
| Column 18, | Lines 4-5, | change "data whilst a user" to --data while a user-- |
| Column 18, | Line 8, | change "Mass transport passenger" to --Mass-transport passenger-- |
| Column 18, | Lines 4-5, | change "data whilst a user" to --data while a user-- |
| Column 18, | Line 28, | change "configurations 206. In these" to --configurations 205. In these-- |
| Column 18, | Line 36, | change "data whilst a user" to --data while a user-- |
| Column 18, | Line 44, | change "due to centralised collection" to --due to centralized collection-- |
| Column 19, | Line 39, | change "then module 510" to --then statistical value determination module 510-- |
| Column 19, | Line 54, | change "of module 510." to --of statistical value determination module 510.-- |
| Column 20, | Line 9, | change "by module 507," to --by trend analysis module 507,-- |
| Column 21, | Line 11, | change "period of time, and are" to --period of time and are-- |
| Column 21, | Line 13, | change "embodiment a user" to --embodiment, a user-- |
| Column 22, | Line 14, | change "application which collects" to --application that collects-- |
| Column 22, | Lines 14-15, | change "data whilst a subject" to --data while a subject-- |
| Column 22, | Line 28, | change "data whilst a subject" to --data while a subject-- |
| Column 22, | Line 32, | change "example, whilst the" to --example, while the-- |
| Column 23, | Line 24, | change "subset that have highest" to --subset that has highest-- |

CERTIFICATE OF CORRECTION (continued)
U.S. Pat. No. 12,159,241 B2

| | | | |
|---|---|---|---|
| | Column 23, | Lines 24-25, | change "of in causational association" to --of in-causational association-- |
| | Column 24, | Line 12, | change "data store and optionally" to --data store 540 and optionally-- |
| | Column 24, | Line 18, | change "stores 505 and/or 509) thereby" to --stores 505 and/or 540) thereby-- |
| | Column 24, | Line 54, | change "containing IMUS. Activity" to --containing IMUs. Activity-- |
| | Column 25, | Lines 7-8, | change "a 5 minute period, 10 minute period, and 1-hour period)" to --a five-minute period, ten-minute period, and one-hour period)-- |
| | Column 25, | Line 21, | change "scoring/percentage based approach" to --scoring/percentage-based approach-- |
| | Column 26, | Line 21, | change "the term coupled, when" to --the term "coupled," when-- |
| In the Claims | | | |
| Claim 1, | Column 27, | Line 19, | change "artifacts which are" to --artifacts that are-- |
| Claim 10, | Column 28, | Line 11, | change "operator of the vehicle;" to --operator of a vehicle;-- |
| Claim 10, | Column 28, | Lines 17-18, | change "data whilst a subject" to --data while a subject-- |
| Claim 10, | Column 28, | Line 18, | change "on the computer;" to --on a computer;-- |
| Claim 10, | Column 28, | Line 32, | change "data whilst a subject" to --data while a subject-- |
| Claim 10, | Column 28, | Line 32, | change "activities on the smartphone/tablet;" to --activities on a smartphone/tablet;-- |